US010100318B2

(12) United States Patent
Babb et al.

(10) Patent No.: US 10,100,318 B2
(45) Date of Patent: Oct. 16, 2018

(54) BIO-FIELD PROGRAMMABLE GATE ARRAY AND BIO-PROGRAMMABLE LOGIC ARRAY: RECONFIGURABLE CHASSIS CONSTRUCTION

(75) Inventors: Jonathan William Babb, Watertown, MA (US); Ron Weiss, Newton, MA (US); Thomas Knight, Cambridge, MA (US); Adam Rubin, Cleveland, OH (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/946,604

(22) Filed: Nov. 15, 2010

(65) Prior Publication Data

US 2011/0257041 A1 Oct. 20, 2011

Related U.S. Application Data

(60) Provisional application No. 61/261,106, filed on Nov. 13, 2009.

(51) Int. Cl.
*C12N 15/63* (2006.01)

(52) U.S. Cl.
CPC .................................. *C12N 15/635* (2013.01)

(58) Field of Classification Search
None
See application file for complete search history.

(56) References Cited

U.S. PATENT DOCUMENTS

| | | | |
|---|---|---|---|
| 5,888,732 A | 3/1999 | Hartley et al. | |
| 7,351,578 B2 | 4/2008 | Cheo et al. | |
| 7,670,823 B1 * | 3/2010 | Hartley | C12N 15/10 435/252.3 |
| 2009/0317910 A1 | 12/2009 | Church et al. | |
| 2010/0267128 A1 * | 10/2010 | Brasch et al. | 435/325 |

OTHER PUBLICATIONS

Invitrogen website, http://products.invitrogen.com/ivgn/product/A10463 , pENTR 2B Dual Selection Description 2013.*

Invitrogen website, http://tools.invitrogen.com/content/sfs/vectors/pentr2b_dual_selection_vecotr_map.pdf , pENTR 2B Dual Selection Vector map, 2013.*

Elowitz et al., Protein mobility in the cytoplasm of *Escherichia coli*. J Bacteriol. Jan. 1999;181(1):197-203.

Hartley et al., DNA cloning using in vitro site-specific recombination. Genome Res. Nov. 2000;10(11):1788-95.

Landy, Dynamic, structural, and regulatory aspects of lambda site-specific recombination. Annu Rev Biochem. 1989;58:913-49.

Mosberg et al., Lambda red recombineering in *Escherichia coli* occurs through a fully single-stranded intermediate. Genetics. Nov. 2010;186(3):791-9. doi: 10.1534/genetics.110.120782. Epub Sep. 2, 2010.

Ohara et al., Directional cDNA library construction assisted by the in vitro recombination reaction. Nucleic Acids Res. Feb. 15, 2001;29(4):E22.

Sauer, Site-specific recombination: developments and applications. Curr Opin Biotechnol. Oct. 1994;5(5):521-7.

Smith et al., Diversity in the serine recombinases. Mol Microbiol. Apr. 2002;44(2):299-307.

Wang et al., Programming cells by multiplex genome engineering and accelerated evolution. Nature. Aug. 13, 2009;460(7257):894-8. doi: 10.1038/nature08187.

* cited by examiner

*Primary Examiner* — Nancy A Treptow

(74) *Attorney, Agent, or Firm* — Wolf, Greenfield & Sacks, P.C.

(57) ABSTRACT

Aspects of the invention relate to reconfigurable chassis that allow for rapid construction and optimization of biocircuits.

23 Claims, 9 Drawing Sheets

Specification includes a Sequence Listing.

Figure 4

This example uses unique overlaps O(1) and O(2) to integrate part 1 (A1,A2) in source plasmid into target 2 (A3,A4) in chromosome.

Example chromosome att sites for target 2 after MAGE modification

Example matching plasmid att sites after MAGE modification

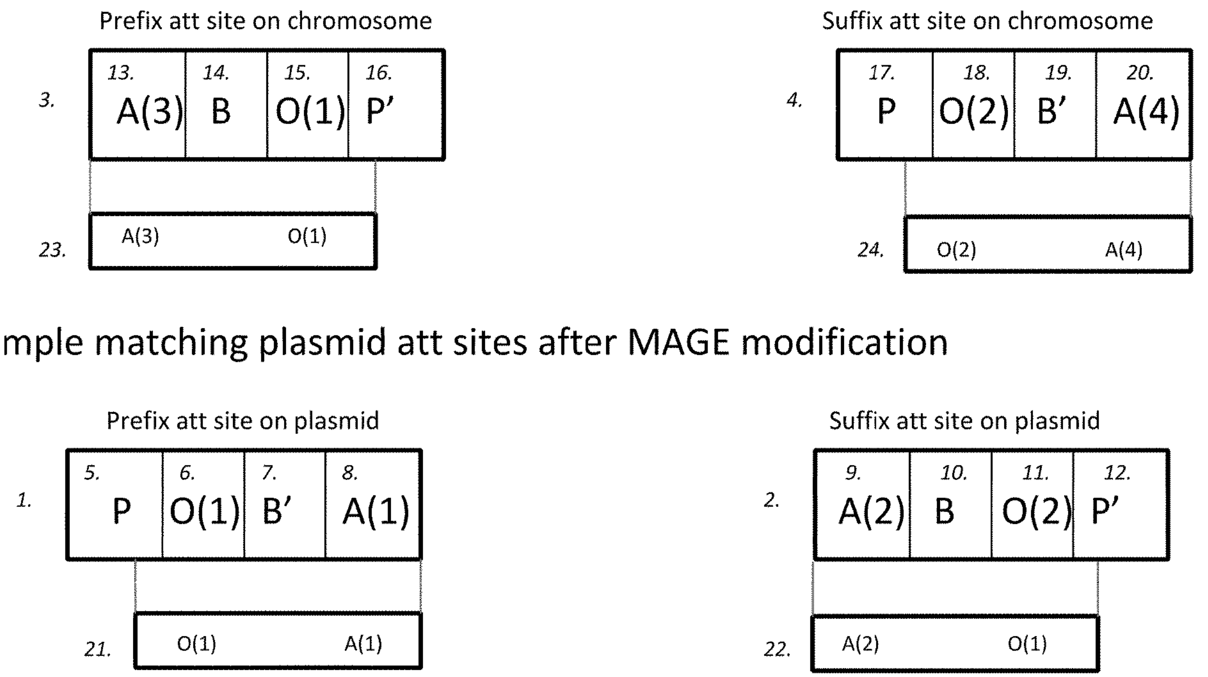

Not shown: additional addressed MAGE oligos to remove stop codons from disabled selection and counterselection markers in chromosome

Figure 8

Design of MAGE oligos

Different unique 65bp addresses for sources and targets: (Ab = address on chromosome, Ap = plasmid)
(these examples are randomly generated with 0.50 GC content; they can be further optimized to remove cloning cutsites and analyze against promoter formation, as is customary by practitioners).

- for target 1 (not used in this example, but must be unique)

Ab(1) GCTAATCGAACTGGGCGAGAGATCCCAGCGCTGATGCACTCGATCCCGAGGCCTGACCCGACATA (SEQ ID NO:38)
Ab(2) TCAGCTCAGACTAGAGCGGGGCTGTTGACGTTTGGGGTTGAAAAAATCTATTGTACCAATCGGCT (SEQ ID NO:39)

- for target 2

Ab(3) GACTTAAGAGTCTATCACCCCTAGGGCCCTTTCCCGGATATAAACGCCAGGTTGAATCCGCATTT (SEQ ID NO:33)
Ab(4) GGAGCTACGATGGATGAGTCTGGGTGGAGCGCGCCCCATTTATACCGTGAGTAGGGTCGACCAAG (SEQ ID NO:34)

- for source 1

Ap(1) AACCGCAAGATGCGTCGGTGTACAAATAATTGTCAACAGACCGTCGTGTTTTGAAAATGGTACCA (SEQ ID NO:35)
Ap(2) GCATCTTCGGGCGGTCTCAATCAAGCATGGATTACGGTGTTTACTCTGTCCTGCGGTTACCCATG (SEQ ID NO:36)

- two different overlaps: O(1) = ATTATAC. (SEQ ID NO:27); O(2) = CTTATAC (SEQ ID NO:26)
- Constants:
  - B = cctgcttt (SEQ ID NO:40)
  - P'= taagttggca (SEQ ID NO:41)
  - P = tcagcttt (SEQ ID NO:42)
  - B'= taacttgagc (SEQ ID NO:43)

Figure 9

Resulting MAGE oligos for example

- Resulting MAGE oligos for chromosome target 2: The * shows a phosphorothioate bond)

- Ab(3):B:O(1):P'=
G*A*CTTAAGAGTCTATCACCCCTAGGGCCCTTTCCCGGATATAAACGCCAGGTTGAATCCGCATTTcctgctttATTATACtaagttgg*c*a
(SEQ ID NO:44)
- P:O(2):B':Ab(4)=
t*c*agctttCTTATACtaacttgagcGGAGCTACGATGGATGAGTCTGGGTGGAGCGCGCCCCATTTATACCGTGAGTAGGGTCGACCA*A*G
(SEQ ID NO:45)

- Resulting MAGE oligos for plasmid source 1:

- P:O(1):B':Ap(1)=
t*c*agctttATTATACtaacttgagcAACCGCAAGATGCGTCGGTGTACAAATAATTGTCAACAGACCGTCGTGTTTTGAAAATGGTAC*C*A
(SEQ ID NO:46)
- Ap(2):B:O(2):P'=
G*C*ATCTTCGGGCGGTCTCAATCAAGCATGGATTACGGTGTTTACTCTGTCCTGCGGTTACCCATGcctgctttCTTATACtaagttgg*c*a
(SEQ ID NO:47)

BIO-FIELD PROGRAMMABLE GATE ARRAY AND BIO-PROGRAMMABLE LOGIC ARRAY: RECONFIGURABLE CHASSIS CONSTRUCTION

RELATED APPLICATIONS

This application claims the benefit under 35 U.S.C. § 119(e) of U.S. Provisional Application Ser. No. 61/261,106, entitled "BioFPGA: A Reconfigurable Chassis," filed on Nov. 13, 2009, the disclosure of which is incorporated by reference herein in its entirety.

GOVERNMENT INTEREST

The invention was made with government support under Grant No. EEC0540879 awarded by the National Science Foundation. The governmet has certain rights in the invention.

FIELD OF THE INVENTION

The invention relates to cellular platforms that support reprogrammable logic.

BACKGROUND OF THE INVENTION

Existing technologies for cloning and recombination of genetic material enable construction of arbitrary DNA sequences. However, these techniques are time-consuming and can be rate-limiting because of the need for multiple sequential steps. The transformation of an existing plasmid into a bacterial host strain can be done rapidly and reliably when a selection marker such as ampicillin is used, however several limitations exist, such as: the number of different plasmids that can be co-transformed is limited by the choice of selection markers and compatible origins of replication; plasmids are less stable than chromosomal DNA and are difficult to maintain indefinitely without mutations occurring; and cistronic interactions cannot be designed since each new nucleotide sequence added is on an unconnected DNA molecule.

SUMMARY OF THE INVENTION

Described herein are novel reconfigurable chassis enabling rapid construction of biocircuits. Based on concepts from digital electronics, classes of chassis described herein are termed Bio-Field Programmable Gate Arrays (BioFPGAs) and Bio-Programmable Logic Arrays (BioPLAs). The BioFPGA chassis is engineered to allow seamless integration of genes and other DNA, while the BioPLA is engineered to enable easy re-wiring of existing synthetic circuits.

Aspects of the invention relate to cells comprising a reconfigurable chromosome engineered to express a series of recombination sites, wherein each recombination site has a unique address, and a series of selection markers. In some embodiments, the cell is a bacterial cell such as an *E. coli* cell. In some embodiments, the recombination sites are att (attachment) sites.

Aspects of the invention relate to Bio-Field Programmable Gate Arrays (BioFPGAs) comprising a biological circuit comprising recombinant DNA engineered to express a series of recombination sites, wherein each recombination site has a unique address, and a series of selection markers. In some embodiments, the recombination sites are att (attachment) sites. In some embodiments, the recombinant DNA is chromosomal DNA while in other embodiments, the recombinant DNA is plasmid DNA.

Further aspects of the invention relate to kits comprising cells and/or BioFPGAs described herein. In some embodiments, the kit further comprises one or more oligonucleotides. In some embodiments, the kit further comprises one or more plasmids.

Further aspects of the invention relate to methods involving: providing a cell comprising a reconfigurable chromosome engineered to express a series of recombination sites, wherein each recombination site has a unique address, and a series of selection markers; conducting multiplex automated genome engineering (MAGE) on one or more of the recombination sites in the reconfigurable chromosome, thereby generating a reconfigured chromosome; providing a plasmid that comprises one or more recombination sites matching the mutated recombination sites on the reconfigured chromosome; and conducting recombination between the plasmid and the reconfigured chromosome.

Further aspects of the invention relate to cells comprising a reconfigurable chromosome engineered to express a biological circuit comprising a set of programmable AND gates linked to a set of programmable OR gates, wherein the biological circuit comprises one or more configuration bits that, when mutated, change the functionality of the biological circuit. In some embodiments, the cell is a bacterial cell, such as an *E. coli* cell.

Aspects of the invention relate to Bio-Programmable Logic Arrays (BioPLAs) comprising a biological circuit comprising recombinant DNA engineered to express a set of programmable AND gates linked to a set of programmable OR gates, wherein the biological circuit comprises one or more configuration bits that, when mutated, change the functionality of the biological circuit. In some embodiments, the recombinant DNA is chromosomal DNA while in other embodiments, the recombinant DNA is plasmid DNA.

Further aspects of the invention relate to kits comprising the cells and/or BioPLAs described herein. In some embodiments, the kit further comprises one or more plasmids.

Further aspects of the invention relate to methods comprising: providing a cell comprising a reconfigurable chromosome engineered to express a biological circuit comprising a set of programmable AND gates linked to a set of programmable OR gates, wherein the biological circuit comprises one or more configuration bits that, when mutated, change the functionality of the biological circuit; and conducting multiplex automated genome engineering (MAGE) on one or more of the configuration bits, thereby changing the functionality of the biological circuit.

These and other aspects of the invention, as well as various embodiments thereof, will become more apparent in reference to the drawings and detailed description of the invention.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4 presents a schematic depicting an example of integration of unique overlaps into a target chromosome. Identifier numbers within the figure correspond to the following: 1: plasmid prefix att site; 2: plasmid suffix att site; 3: chromosome prefix att site; 4: chromosome suffix att site; 5-20: similar parts to previous figures for chromosome and plasmid; 21-24: mage oligos to introduce specific overlap mutation in att sites. Non-limiting possible sequences for O(1) and O(2) include: TTTATAC (SEQ ID NO:24), TTTGTAC (SEQ ID NO:25), CTTATAC (SEQ ID NO:26), ATTATAC (SEQ ID NO:27), TCTATAC (SEQ ID NO:28), TGTATAC (SEQ ID NO:29), TTCGTAC (SEQ ID NO:30), TTGGTAC (SEQ ID NO:31), TTAATAC (SEQ ID NO:32). Non-limiting examples of unique address for A(1), A(2), A(3) and A(4) include:

```
                                          (SEQ ID NO: 33)
GACTTAAGAGTCTATCACCCCTAGGGCCCTTTCCCGGATATAAACGCC
AGGTTGAATCCGCATTT;

                                          (SEQ ID NO: 34)
GGAGCTACGATGGATGAGTCTGGGTGGAGCGCGCCCCATTTATACCGT
GAGTAGGGTCGACCAAG;

                                          (SEQ ID NO: 35)
AACCGCAAGATGCGTCGGTGTACAAATAATTGTCAACAGACCGTCGTG
TTTTGAAAATGGTACCA;
and

                                          (SEQ ID NO: 36)
GCATCTTCGGGCGGTCTCAATCAAGCATGGATTACGGTGTTTACTCTG
TCCTGCGGTTACCCATG.
```

Figure 5:
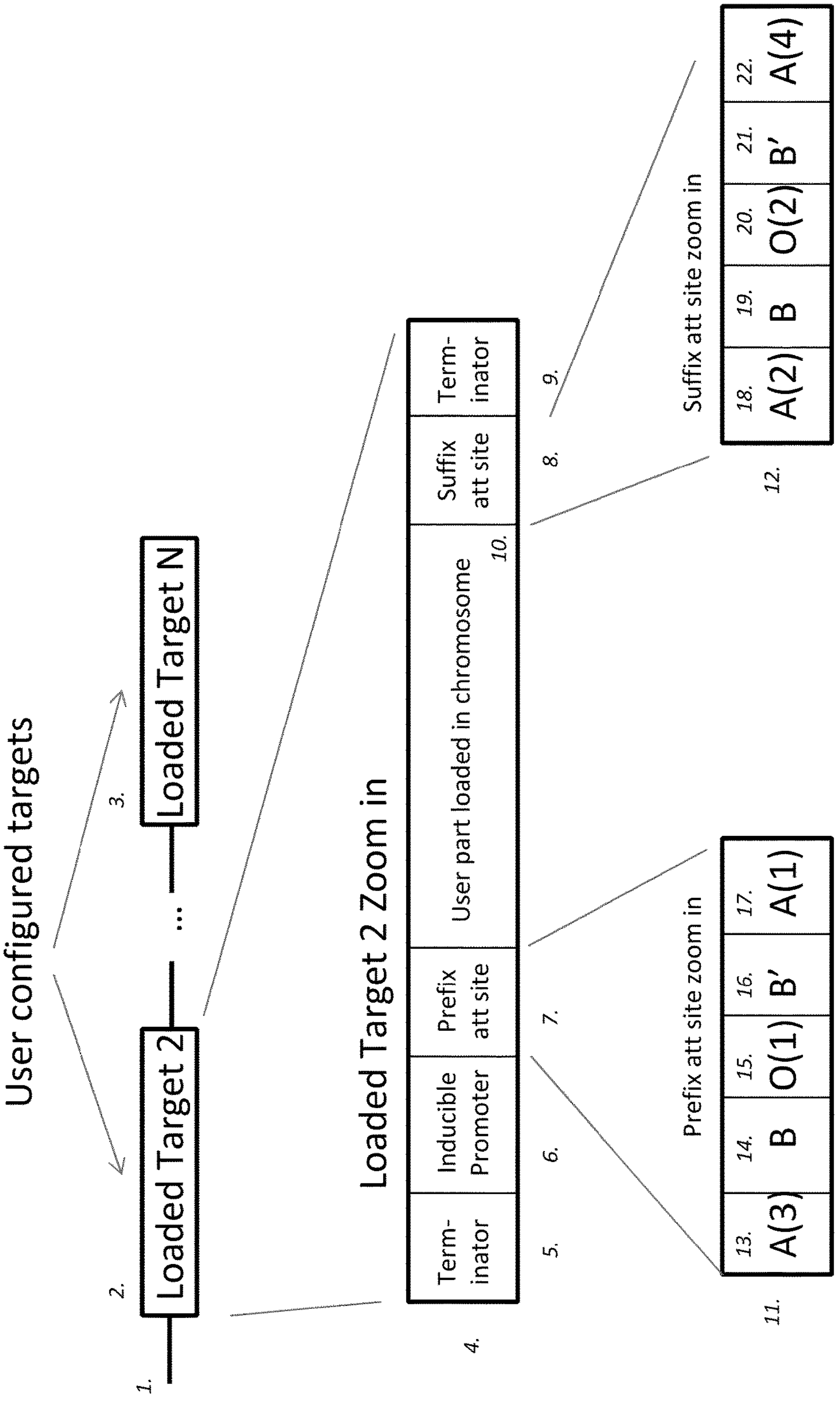

FIG. 5 presents a schematic depicting user configured targets. Identifier numbers within the figure correspond to the following: 1: chromosomal DNA; 2-3: loaded user configurable target sites in chromosome; 4: loaded target 2 zoom in; 5-9: see previous figures; 10: user part selected from source plasmid library, now loaded into target zone; 11-12: zoom in of att sites; 13-22: shows ordering of addressing, attB, attP, and overlap regions in att sites.

Figure 6:
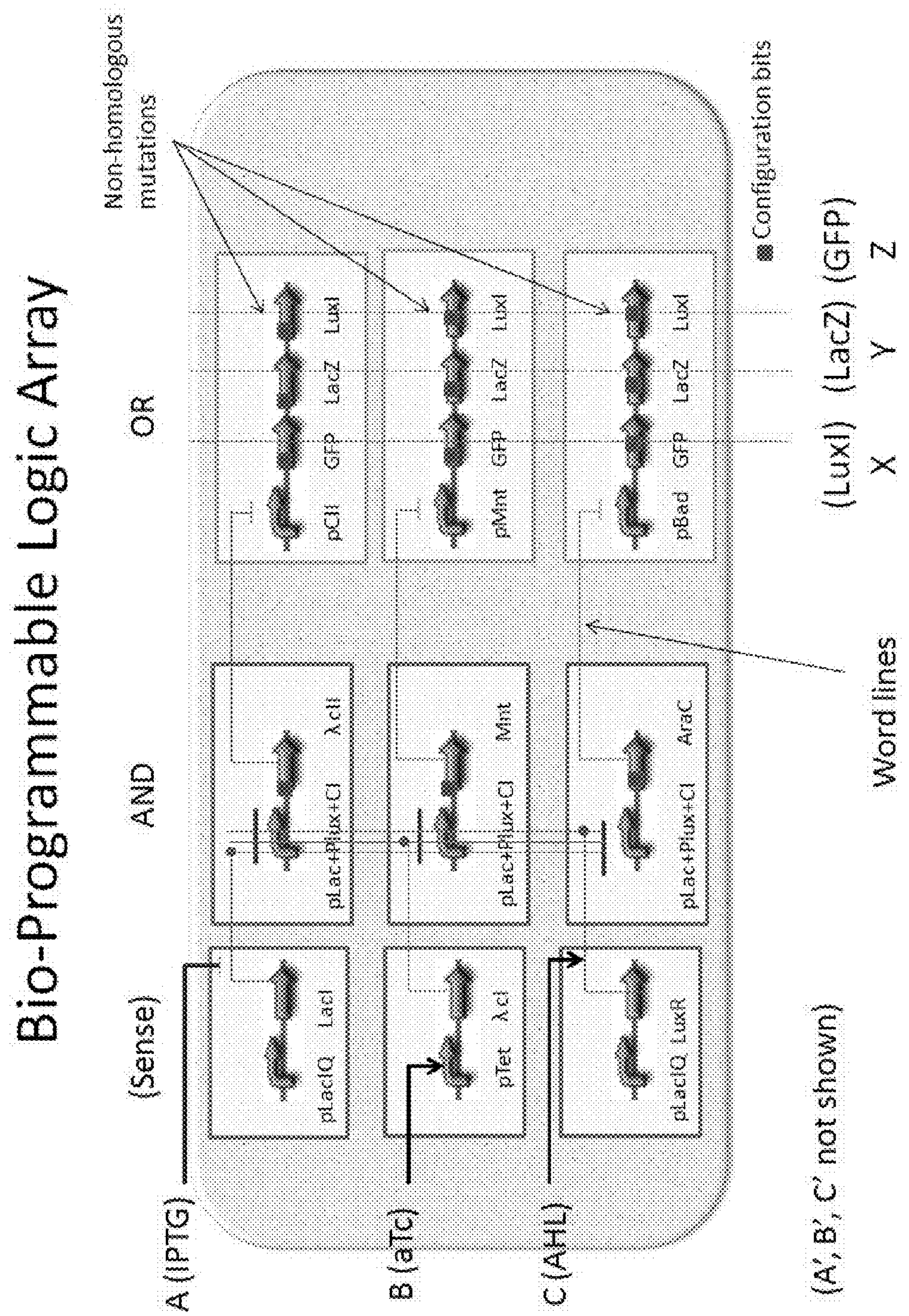

FIG. 6 presents a schematic depicting a Bio-Programmable Logic Array (BioPLA). Identifier numbers within the figure correspond to the following: 1: outer oval represents an *E.coli* cell; 2: within each set of arrows (each contained within a square), the left-most arrow is a promoter, while the remaining arrows are genes; 3: the dot (small square) indicated on several of the genes is a configuration bit created by adding/removing a stop codon with MAGE oligos; 4: IPTG=Isopropyl β-D-1-thiogalactopyranoside; 5: aTC=anhydrotetracycline (ATc) is a tetracycline analog; 6: AHL=3-oxo-C6-HSL; 7: pLaqIQ=a constitutive promoter; 8: pTet=promoter repressed by tetR (tetR gene not shown); 9: lcII=gene from lambda phage that represses pCII; 10: Mnt=gene that represses pMnt; 11: AraC=gene that represses AraC; 12: pCII=promoter repressed by lcII gene; 13: pMnt=promoter repressed by Mnt; 14: pBad=repressed by AraC; 15: GFP=green fluorescent protein reporter; 16: LacZ=gene used as a reporter with X-gal; 17: LuxI=gene that produces AHL; 18: pLac+pLux+pCI; 19: A', B', and C' refer to the inverse or NOT signals of the inputs, which are also required in the circuit for a full PLA implementation; 20: the PLA is divided into an AND plane and an OR plane connected by word lines; 21: non-homologous mutation: applying MAGE to the same gene in different locations requires non-homology. Each gene instance can be codon optimized, the mutation can be at different locations in the gene, or there can be an address/barcode region added to the start or end of each gene.

Figure 7:
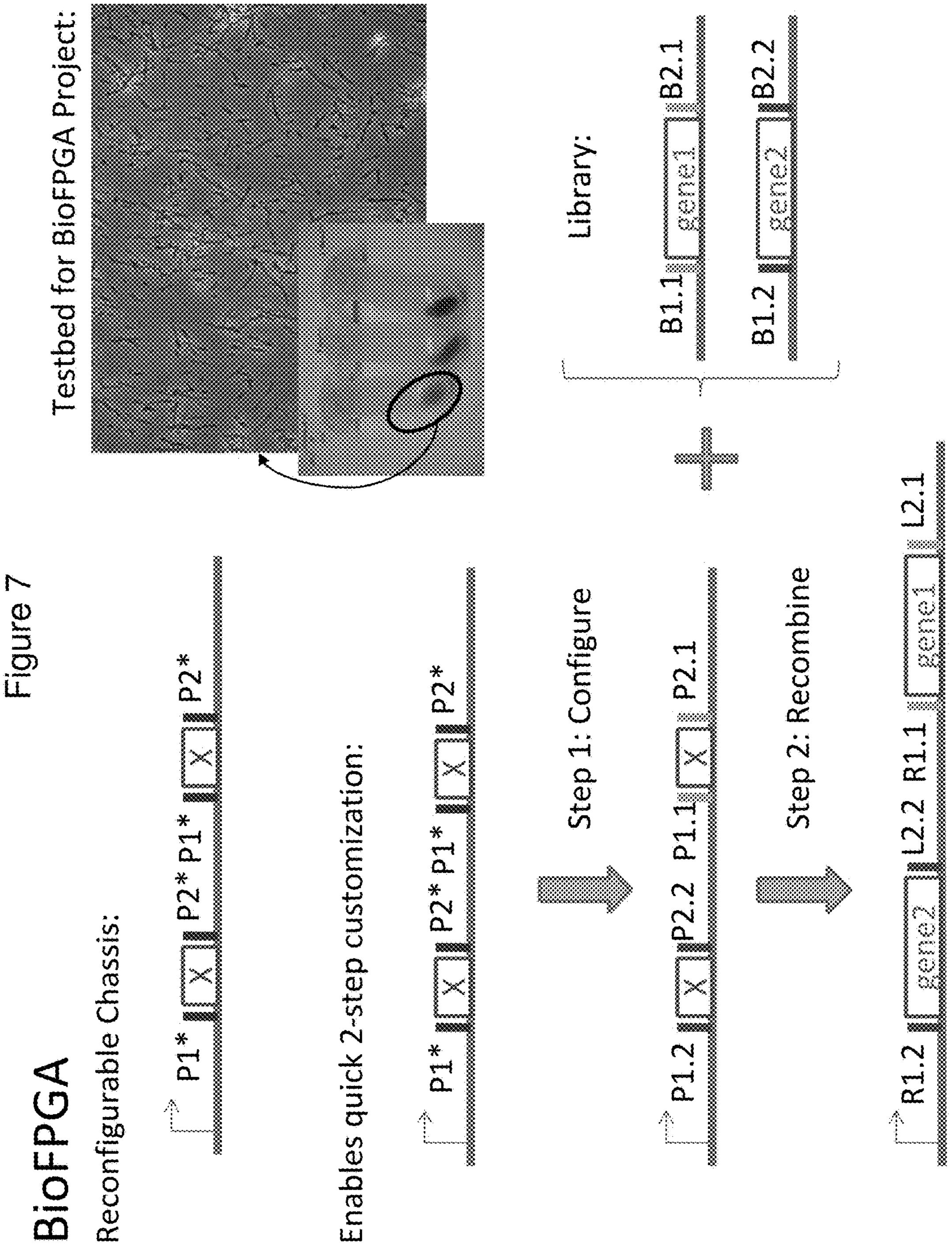

FIG. 7 presents a schematic depicting a Bio-Field Programmable Gate Array (FPGA). Identifier numbers within the figure correspond to the following: 1: a version of the BioFPGA based on BP recombination (attB x attP); 2: this reconfigurable chassis consists of promoter (arrow) followed by two pairs of att sites (in this case attP, shown as boxes and labeled P1* and P2*) to allow insertion of genes (boxes with X to designate any gene can go there). Not shown in the figure: each P1 and P2 can be uniquely addressed on the chromosome. The promoter demonstrates a fixed portion of the circuit which is not reconfigured; 3: on the lower right is a library of two genes, enclosed by attB sites; 4: the configuration step involves mutating the unique overlap regions of the attP sites to match the attB sites in the genes to be inserted; 5: the recombination step involves inducing lambda phage Integrase (Int) (not shown), integrating the genes into the chromosome in the designated locations, such that the four numbered overlap regions match (1.1, 1.2, 2.1, 2.2). Note the attachment sites becomes attL and attR sites; 6: top right figure shows a testbed circuit constructed for the BioFPGA project which will allow a GFP gene to be configured to be always on or function as an inverter when induced with AHL.

FIG. 8 presents an overview of MAGE oligonucleotide design.

FIG. 9 presents several examples of MAGE oligonucleotides.

DETAILED DESCRIPTION OF THE INVENTION

Aspects of the invention relate to reconfigurable chassis, termed Bio-Field Programmable Gate Arrays (BioFPGAs) and Bio-Programmable Logic Arrays (BioPLAs). The chassis described herein represent cellular platforms with reconfigurable architectural features that support multiple uses. BioFPGA devices provide specific structures and scaffolding, enabling recombination of genetic elements. With this approach, a new biocircuit can be constructed rapidly without requiring any plasmid design or DNA assembly by the end user. BioPLA devices enable rapid re-wiring of existing synthetic circuits. The configuration approaches described herein enable technology for the rapid exploration of new biocircuits.

This invention is not limited in its application to the details of construction and the arrangement of components set forth in the following description or illustrated in the drawings.

The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the invention relate to reconfigurable chassis. As used herein, a "chassis" refers to a framework or structure that can support multiple uses. As used herein, "reconfigurable" means that the chassis can be configured differently by each end user to achieve different functions. Thus, reconfigurable chassis described herein provide significant acceleration of DNA cloning and biocircuit construction and/or optimization by providing a pre-configured framework or structure that can be reconfigured by the end-user.

In some aspects, the reconfigurable chassis is termed a BioFPGA (Bio-Field Programmable Gate Array). An FPGA (Field Programmable Gate Array), in electronics, is an integrated circuit designed to be configured by the customer or designer after manufacturing. As used herein, a BioFPGA refers to an FPGA in which the integrated circuit is a biological circuit. As used herein, a "biological circuit" refers to a configuration of connected biological components. Biological components of biocircuits can be comprised of nucleic acids. As used herein, a "nucleic acid" refers to a macromolecule composed of chains of nucleotides. In some embodiments, nucleic acids are DNA, RNA or PNA.

A BioFPGA can comprise recombinant DNA engineered to express a series of recombination sites and a series of selection markers. In some aspects, a Bio-FPGA comprises chromosomal DNA such as bacterial chromosomal DNA. In certain embodiments, a Bio-FPGA comprises *E. coli* chromosomal DNA. In other embodiments, a Bio-FPGA comprises plasmid DNA.

The recombination sites within the BioFPGA are compatible for conducting site-specific recombination or recombinational cloning. As used herein, "recombination," "site-specific recombination" and "recombinational cloning" are used interchangeably to refer to an exchange of regions from two different DNA molecules. Generally, site-specific recombination is achieved by means of enzymes which recognize particular short sequences that represent sites of recombination.

Principles and methods for site-specific recombination and recombinational cloning are discussed further in, and incorporated by reference from, U.S. Pat. No. 5,888,732 (Hartley et al.); U.S. Pat. No. 7,351,578 (Cheo et al.); Hartley et al., "DNA Cloning Using In Vitro Site-Specific Recombination," (2000) *Genome Research* 10:1788-1795; and Ohara et al., "Directional cDNA library construction assisted by the in vitro recombination reaction," (2001) Nucleic Acids Research 29, No. 4 e22.

In some embodiments, the recombination sites are att (attachment) sites, such as attB, attP, attL and attR sequences, based on the bacteriophage lambda recombination system. Bacteriophage lambda contains an attP site that can recombine with an attB site within an *E. coli* chromosome, mediated by the protein integrase. Use of att sites for in vitro site-specific recombination has been demonstrated through the Gateway® technology from Invitrogen (Carlsbad, Calif.). attB sites are approximately 25 bp, while attP sites are approximately 240 bp. In other embodiments, other tyrosine recombinase systems such as Cre-Lox or Dre-Rox are used. In some embodiments, the recombination sites are loxP sites for the Cre recombinase. The loxP recombination site is described in Sauer (1994) *Curr. Opin. Biotech* 5:521-527, as a 34 base pair sequence including two 13 by inverted repeats. In some embodiments, the recombination system is a site-specific serine recombinase system (Smith et al., (2002), "Diversity in the serine recombinases," 44(2), 299-307). It should be appreciated that other recombination systems can be compatible with aspects of the invention, as would be understood by one of ordinary skill in the art.

Aspects of the invention relate to engineering of recombination sites, such as att sites. Each att site contains two 9 by core-type Int binding sites and a 7 by overlap region (Landy (1989), *Ann. Rev. Biochem.* 58:913). att sequences can be mutated as long as the identity between the two sequences to be recombined is maintained. In some embodiments, recombination efficiency between att sites is improved by mutating the att sites, for example to remove stop codons that occur within the att sites. Thus, att sites can be engineered to contain one or more mutations. Methods and principles associated with engineering of att sites are discussed further in, and incorporated by reference from, U.S. Pat. No. 5,888,732 (Hartley et al.) and U.S. Pat. No. 7,351,578 (Cheo et al). In some embodiments, sequences to be recombined according to aspects of the invention, have identical 7 by overlap regions.

Each recombination site within the BioFPGA is provided with a unique address. For example, in some embodiments, if the recombination site is an att site, such as an attB site, a sequence is added before or after the attB site, providing a unique address for that recombination site. The length of the unique address can vary depending on the circumstances. In some embodiments, the unique address is approximately 65 bps. In some embodiments, the unique address is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 bps. Unique addresses are designed such that no two addresses will have a high sequence similarity. In some embodiments, the unique address is added to the BioFPGA using MAGE (multiplex automated genome engineering). Principles and procedures for conducting MAGE are described further in, and incorporated by reference from, U.S. Patent Publication No. US 2009/0317910 (Church et al.) and Wang et al., "Programming cells by multiplex genome engineering and accelerated evolution," (2009) *Nature* 460:894-898.

Recombination sites within a BioFPGA surround selection and/or counterselection markers. Non-limiting examples of selection markers include antibiotic resistance markers, such as markers that confer resistance to ampicilin, chloramphenicol, kanamycin or tetracycline. Non-limiting examples of counterselection markers include ccdB, sacB, mazF and pheS. It should be appreciated that a wide variety of selection markers are compatible with aspects of the invention, as would be understood by one of ordinary skill in the art.

Figure 1:
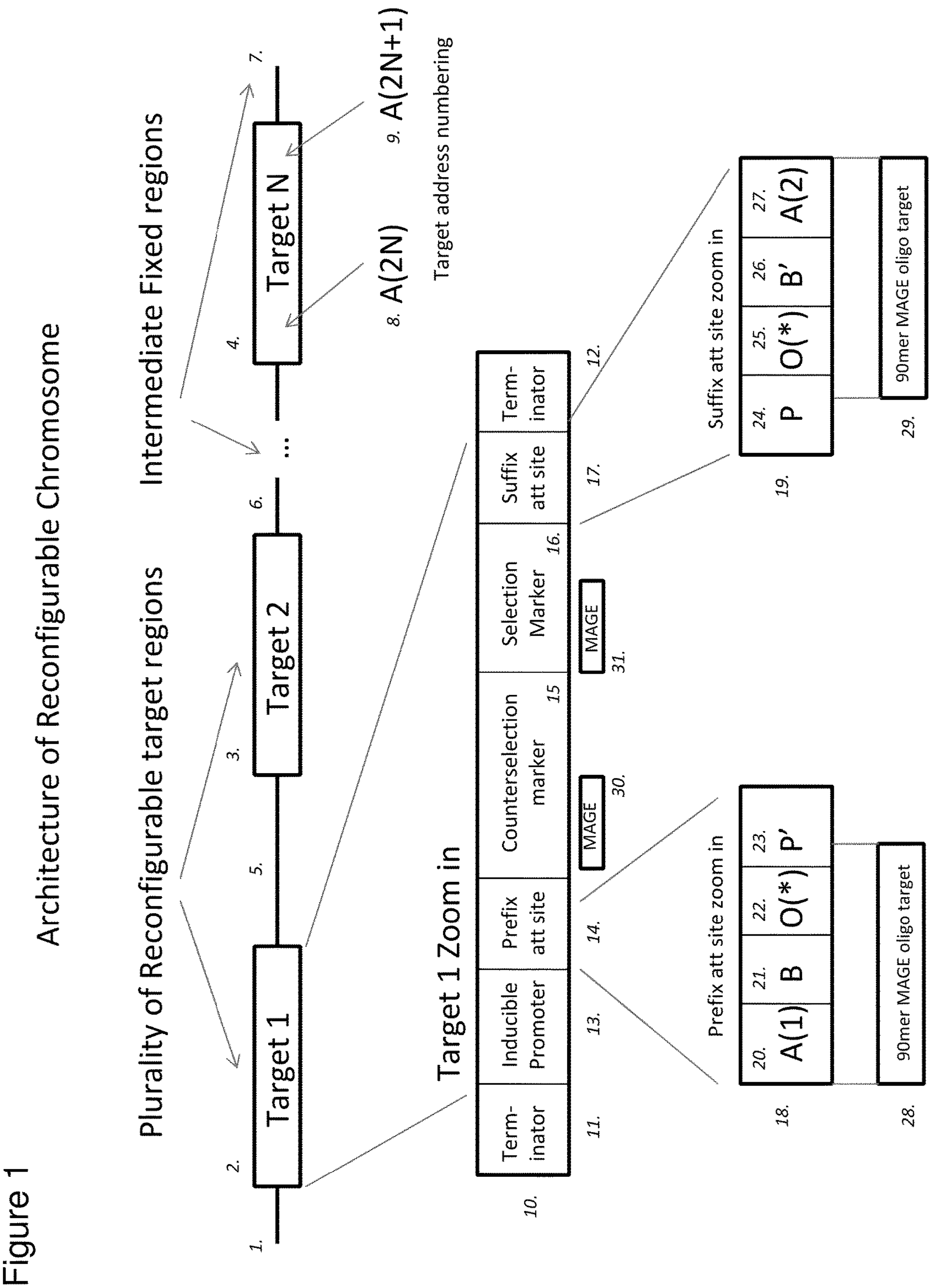
FIG. 1 presents a schematic of a reconfigurable chromosome. Identifier numbers within the figure correspond to the following: 1: chromosomal DNA; 2-4: target reconfigurable regions integrated into chromosomal DNA; 5-7: fixed regions of natural and /or synthetic DNA; 8-9: unique address numbering for the prefix and suffix attachment sites of each target region; 10: zoom in of target region 1; 11-12: terminators to prevent leaky induction and isolate target region; 13: inducible promoter, e.g., pBAD (arabinose inducible); 14: attachment site preceding the reconfigurable zone; 15: counterselection marker, such as ccdB; 16: optional selection marker, such as bla (ampicillin); 17: attachment site following the reconfiguration target zone; 18-19: zoom in of attachment sites; 20: 65 bp unique address for prefix attachment site; 21: Bacterial attachment site (attB) sequence following overlap region (TAACTTGA; SEQ ID NO:21); 22: default overlap sequence (TTTTATAC; SEQ ID NO:22); 23: phage attachment site (attP) sequence preceding overlap region (same as wt lambda); 24: phage attachment site (attP) sequence following overlap region (same as wt lambda); 25: default overlap sequence (TTTTATAC; SEQ ID NO:22); 26: Bacterial attachment site (attB) sequence preceding overlap region (AGCCTGCTTT; SEQ ID NO:23); 27: 65 bp unique address for suffix attachment site; 28-29: location of homology between 90mer MAGE addressing oligos and attachment sites; 30-31: MAGE targets to turn on counterselection and selection markers (unique address prefix for markers not shown).

A non-limiting example of a reconfigurable chromosome, as an embodiment of a BioFPGA, is shown in FIG. 1. The reconfigurable chromosome contains multiple regions that can be targeted for recombination. Target 1, representing a non-limiting example of a target region, contains multiple nucleic acid sequences including a terminator sequence, an inducible promoter sequence, a prefix att site, a counterselection marker, a selection marker, a suffix att site and another terminator sequence. The two att sites surrounding the counterselection and selection markers are demonstrated to contain unique addresses, indicated as "A(1)" and "A(2)." Homology between MAGE oligonucleotides and the att sites is also shown. In some embodiments, a MAGE oligonucleotide is approximately 90 bp.

In some embodiments, MAGE is applied to all att sites, with one oligonucleotide per att site. In other embodiments, bases outside of the overlap region of the att site are modified to reduce recombination efficiency. In some embodiments, the MAGE step restores the att site (correcting the recombination efficiency) and assigning the overlap region.

Aspects of the invention relate to reconfiguration of a BioFPGA and recombination of specific genes or other genetic elements into the BioFPGA. Specific genes or other genetic elements can be inserted into a BioFPGA using site-specific recombination. For example, a specific gene or other genetic element can be provided in a plasmid such as in a library of plasmids, where each gene or genetic element in a given plasmid is flanked by recombination sites. In some embodiments, the recombination sites in both the BioFPGA and the plasmid are att sites. In some embodiments, in order to create specificity in the recombination event, att sites can be mutated such that one specifically mutated att site will only recombine with other att sites that have a similar mutation. Specific mutations in att sites can be generated by MAGE.

In some embodiments, it is not necessary to perform MAGE on a plasmid to be recombined because a plasmid library can contain more than one copy of each sequence to be recombined. In some embodiments, multiple versions of a plasmid containing a given sequence to be recombined exist in a library and each version of the plasmid contains different recombination sequences. Each version can have a different pair of overlap regions. For example, if there are two target locations and four overlap regions (1,2 and 3,4), then there would be a 1---part---2 and a 3---part---4 version of each part to enable it to go in each location, wherein a "part" refers to a region to be recombined. In some embodiments, not every part needs to be assignable to every location, but if that is desired, it would entail an N×M total library size, where N is number of parts and M is number of targets.

In other embodiments, MAGE is conducted on the plasmid to establish the unique address of the plasmid to be recombined. In some embodiments, MAGE oligonucleotides recombine and change the overlap regions of the plasmid att sites. In some embodiments, MAGE is not used for plasmids if the copy number is greater than 1 because only a portion of the plasmids will be mutated and would require selection. However, only one copy needs to be mutated since only the mutated one will attempt to recombine with the matching mutated att sites on the chromosome. Counterselection will allow that only cells in which all events have occurred will be maintained (events=MAGE of left and right att site on each part in at least one copy of the source plasmid(s), MAGE of left and right att site on the target chromosome, and then successful recombination. These 5 events for each target site must occur, or the counterselection marker will kill the cell when induced).

Without wishing to be bound by any theory, the recombination event is a strand exchange so when the selection and counterselection markers are moved back to the plasmid they should not be transcribed from that location. In some embodiments, steps can be taken in order to ensure that nothing is transcribed from that region. Several non-limiting examples of such steps that can be taken include: terminators can be added outside the att sites, strong promoters can be avoided and frameshifts can be introduced. In some embodiments, a single plasmid can contain more than one part to be recombined, or multiple plasmids can be co-transformed in parallel wherein each plasmid contains one or more parts to be recombined. In some embodiments, target sites can be loaded sequentially, such that one plasmid is introduced, then that plasmid is cured, then a second plasmid is transformed, etc. In some embodiments, the source of DNA to be recombined into a reconfigurable chromosome does not come from a plasmid, but rather comes from another location on the chromosome.

Figure 2:
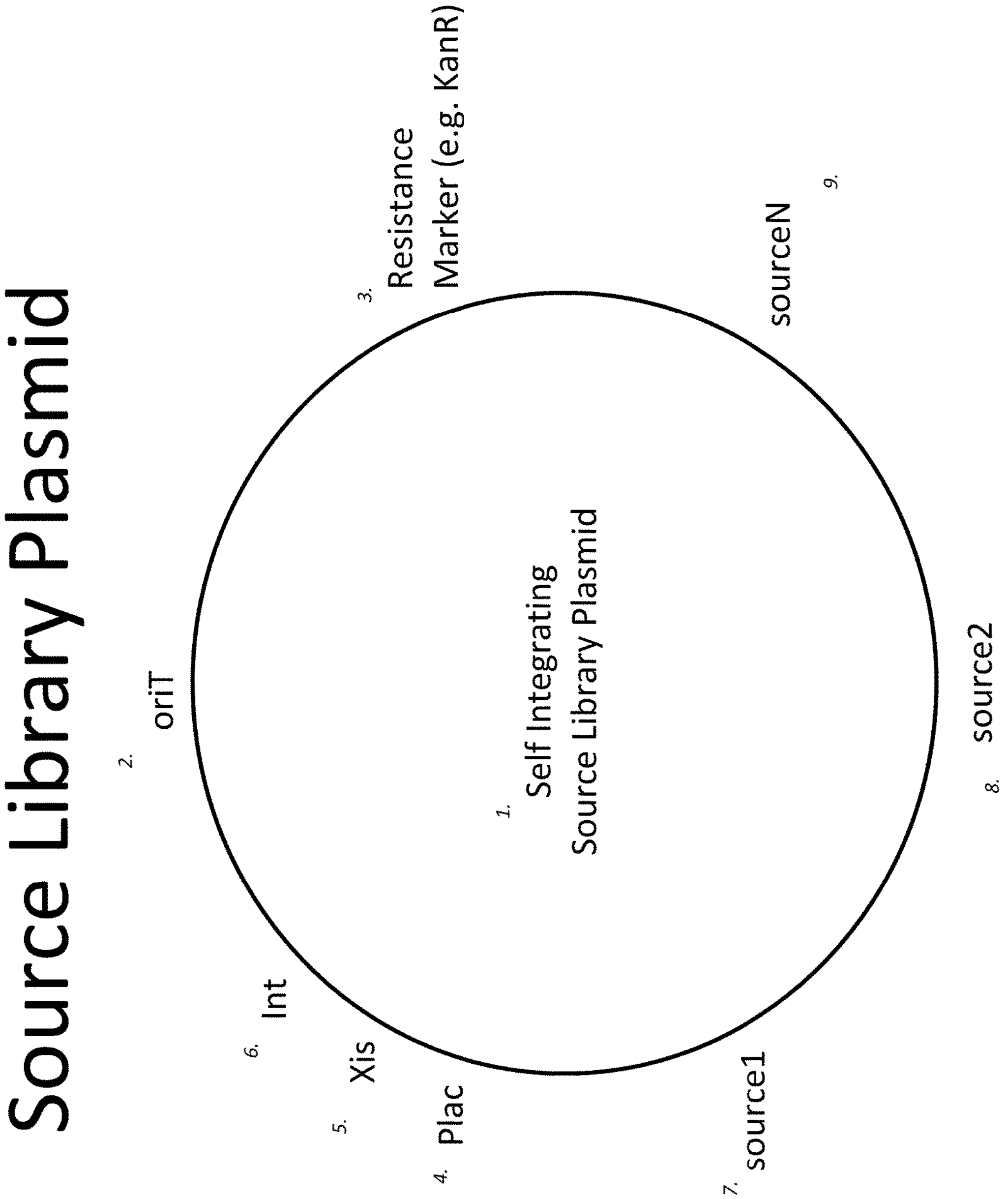
FIG. 2 presents a schematic of a non-limiting example of a source library plasmid. Identifier numbers within the figure correspond to the following: 1: self integrating plasmid of source library parts; 2: origin of replication, for example PUC19; 3: resistance marker to stably transform this plasmid (e.g. KanR); 4: an example of an IPTG Inducible promoter for Xis/Int expression; 5: Lambda excisase gene (wild type); 6: Lambda integrase gene (wild type); 7-9: source library cassettes (see FIG. 3 for details).
Figure 3:
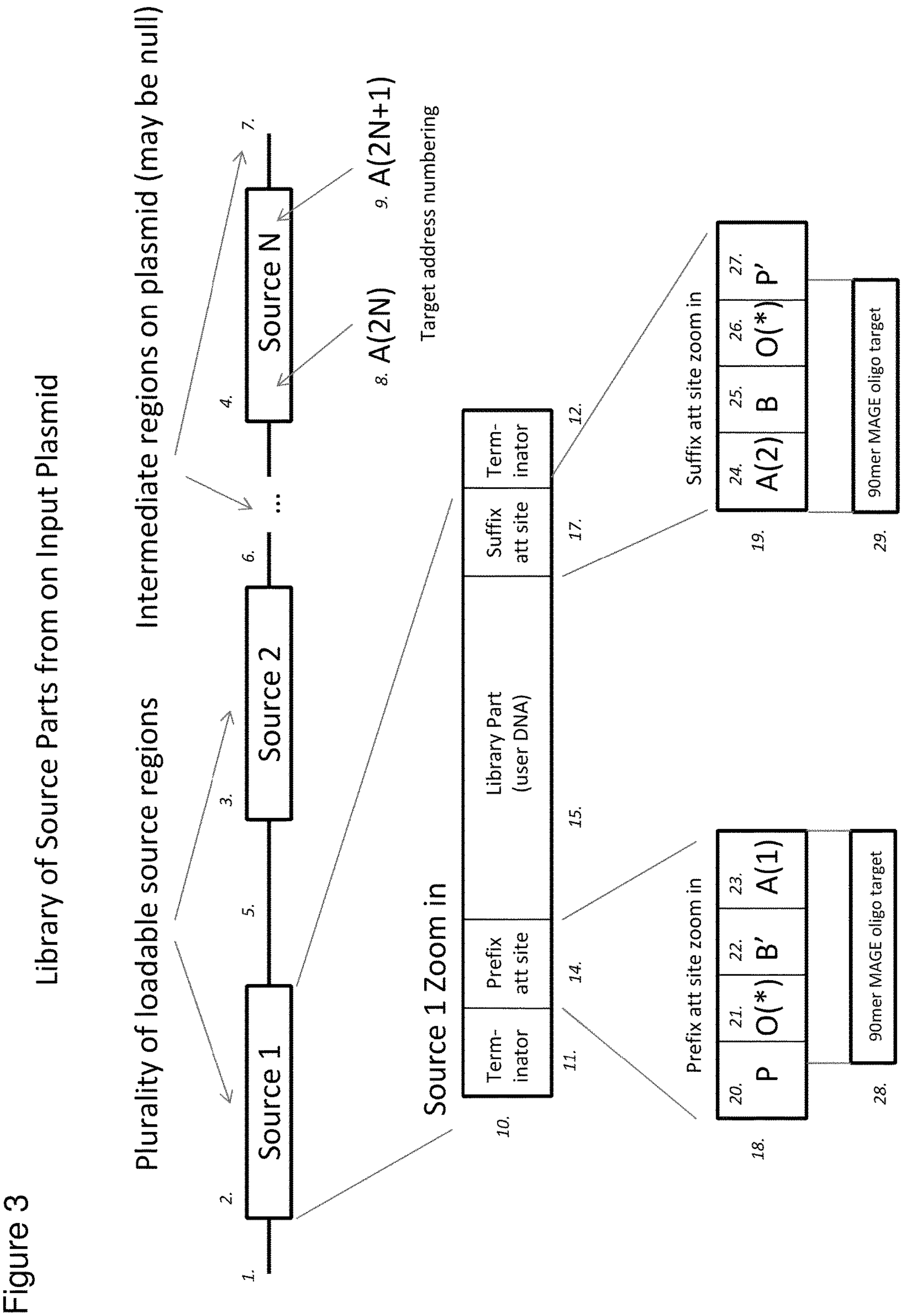
FIG. 3 presents a schematic depicting a library of source parts from an input plasmid. Identifier numbers within the figure correspond to the following: 1: plasmid DNA; 2-4: source regions to be integrated into chromosomal DNA; 5-7: possible intermediate regions in source plasmid; 8-9: unique address numbering for the prefix and suffix attachment sites of each source region; 10: zoom in of source region 1; 11-12: terminators to prevent expression of source DNA from plasmid or counterselector after recombination; 13: unused number; 14: attachment site preceding the source part; 15: source library part; 16: unused number; 17: attachment site following the source part; 18-19: zoom in of attachment sites; 20: Phage attachment site (attP) sequence preceding overlap region (same as wt lambda); 21: default overlap sequence (TTTTATAC; SEQ ID NO:22); 22: Bacterial attachment site (attB) sequence following overlap region (TAACTTGA; SEQ ID NO:21); 23: 65 bp unique address for prefix attachment site; 24: 65 bp unique address for suffix attachment site; 25: Bacterial attachment site (attB) sequence preceding overlap region (AGCCTGCTTT; SEQ ID NO:23); 26: default overlap sequence (TTTTATAC; SEQ ID NO:22); 27: Phage attachment site (attP) sequence following overlap region (same as wt lambda); 28-29: location of homology between 90mer MAGE addressing oligos and attachment sites.

An example of a self integrating source library plasmid is shown in FIG. 2. An example of a library of source parts from an input plasmid is shown in FIG. 3. att sites are shown surrounding a library part to be recombined and homology of oligonucleotides for MAGE to these att sites is shown. FIG. 4 presents a schematic example of a recombination event occurring between chromosomal and plasmid att sites. In this example, part 1 (with addresses A1 and A2) is integrated into target region 2 (with addresses A3 and A4) through unique overlaps O(1) and O(2). In some embodiments, additional MAGE oligonucleotides are used to remove stop codons from disabled selection and counterselection markers in the chromosome. Several non-limiting examples of specific overlap sequences include: TTTATAC (SEQ ID NO:24), TTTGTAC (SEQ ID NO:25), CTTATAC (SEQ ID NO:26), ATTATAC (SEQ ID NO:27), TCTATAC (SEQ ID NO:28), TGTATAC (SEQ ID NO:29), TTCGTAC (SEQ ID NO:30), TTGGTAC (SEQ ID NO:31), TTAATAC (SEQ ID NO:32). Non-limiting examples of unique address for A(1), A(2), A(3) and A(4) include: GACTTAAGAGTCTATCACCCCTAGGGCCCTTTCCCGGA TATAAACGCCAGGTTGAATCCGCATTT (SEQ ID NO:33); GGAGCTACGATGGATGA GTCTGGGTGGAGCGCGCCCCATTTATACCGTGAGTAGGGTCGACCAAG (SEQ ID NO:34); AACCGCAAGATGCGTCGGTGTACAAATAATTGTCAACA GACCGTCGTGTTTTGAAAATGGTACCA (SEQ ID NO:35); GCATCTTCGGGCG GTCTCAATCAAGCATGGATTACGGTGTTTACTCTGTCCTGCGGTTACCCATG (SEQ ID NO:36). FIG. 5 presents a schematic depicting a user-configured chromosome wherein two targets have been recombined into the chromosome.

FIG. 7 presents a schematic of a Bio-FPGA in which a reconfigurable chassis is customized through a two step procedure involving configuration and recombination, resulting in two genes from a library being recombined onto the reconfigurable chassis. Thus, in some embodiments, an end-user provided with a Bio-FPGA undertakes a two step procedure. In the first step, the BioFPGA is reconfigured, for example through the use of MAGE to create specific mutations in recombination sites such as att sites. In the second step, specific genes or genetic elements contained within one or more plasmids are recombined into the BioFPGA. In some aspects, plasmids for use with a BioFPGA are contained within plasmid libraries, wherein each plasmid within the library contains one gene or other genetic element, surrounded by recombination sites. As used herein, a plasmid library refers to a collection of more than one plasmid. In other embodiments, an individual plasmid is provided that contains the gene or genetic element of interest.

In some aspects, the reconfigurable chassis is termed a BioPLA (Bio-Programmable Logic Array). A programmable logic array (PLA), in electronics, refers to a programmable device used to implement combinatorial logic circuits. In some embodiments, a PLA comprises a set of programmable AND gates, which link to a set of programmable OR gates, leading to production of an output. As used herein, a BioPLA refers to a PLA in which the circuits are biological circuits. In some embodiments, a BioPLA comprises a set of reconfigurable AND gates linked to a series of configurable OR gates. A logic gate, such as an AND or OR logic gate, can have one or more inputs and one or more outputs. In some embodiments, each input and/or output is represented by one of two binary conditions: low (0) or high (1). In certain embodiments, an input or output can be measured as the identity of a molecule, the intensity (e.g., level) of output, the duration of expression or increased expression, or any combination thereof. In some embodiments, the set of reconfigurable AND gates and reconfigurable OR gates is linked to series of IDENTITY gates, also referred to as "sense" gates or circuits, wherein these biocircuits detect the presence or absence of an input signal.

It should be appreciated that an input signal can be any signal to which a biocircuit is capable of responding. The input signal will vary depending on the biocircuit. In some embodiments, an input signal is a diffusible molecule. An input signal can be an organic molecule or an inorganic molecule. Non-limiting examples of molecules that can serve as input signals in biocircuits include IPTG, aTc, pheromones such as yeast pheromones including, for example, Sc alpha-factor or Ca alpha factor, biomolecules such as lactones including, for example AHL (acyl-homoserine lactone), phosphoserine or cytokines, small molecules such as doxicycline or methionine, heavy metals such as copper, sugars such as glucose or galactose, and chemical inhibitors. In some embodiments, an input signal can be a physical signal that is not mediated by a specific molecule, for example, temperature (e.g., an increase or decrease in temperature), radiation (e.g., photons or gamma radiation), electromagnetic radiation such as ultraviolet radiation, magnetic force or electrical stimulation.

BioPLAs associated with aspects of the invention contain one or more configuration bits.

As used herein, "configuration bits" refer to regions of the BioPLA that can be reconfigured by the end user. A configuration bit can comprise a region of DNA, as small as a single bp, that if mutated, will change the functionality of the circuit. In some embodiments, MAGE is employed by the end user to change the configuration bits. Thus, the BioPLA enables a sensor or other biocircuit to form outputs from a logical combination of inputs in a programmable fashion. The end user of a BioPLA can change the relationship of the outputs to the inputs. As in electronics, a BioPLA can include memory such that the output can be a function of previous inputs. Thus, the BioPLA enabled re-wiring of synthetic circuits.

The pre-designed circuit allows for many phenotypes, transfer functions from inputs to outputs, to be realized with the same chromosome. In some embodiments, MAGE is used to change the biocircuit by turning on or off an element or by rewiring an element. In some embodiments, parts of the circuit can be on a plasmid. For example, genes or other genetic elements expressed on plasmids can include genes that need to be expressed for other genes in the circuit to work, such as LacI, LuxR or TetR, but which themselves are not intended to be turned on or off during reconfiguration of the chromosome.

FIG. 6 presents an example of a BioPLA. In some embodiments, promoters of components within the circuit, such as the pLac+PLux+CI promoters, can be mutated to respond to specific inputs or combinations of inputs (such as 0, 1, 2 or 3 inputs). For example this could be addressed with one MAGE oligonucleotide for the −10 region and one for the −35 region.

In some embodiments, configuration of a bit in a BioPLA can comprise one or more of the following: adding a stop codon at the start of a gene to deactivate the gene, changing the strength of a promoter such that it is stronger, weaker, or disabled altogether relative to the strength of the promoter prior to configuration of the bit, changing a promoter to make it sensitive or not sensitive to a repressor or activator, changing the strength of a ribosome binding site, making a small mutation on a gene, for example to make it more or less sensitive to a condition, or changing a region to be targeted by interfering RNA. In some embodiments, non-homologous codon optimized versions of sequences are used.

In some embodiments, principles of the BioPLA can be applied to incrementally change genetic elements in the BioFPGA. For example, the ribosome binding site strength of genes can be changed through MAGE. In some embodiments, the BioFPGA recombination is used to add one or more genes to a reconfigurable chromosome and then the ribosome binding site strength of each gene can be tuned with a further configuration oligonucleotide through the use of MAGE. In some embodiments, all user genes can be in the "off state," with stop codons near their start, during construction, recombination and circuit configuration. Then a final MAGE round can turn on the user genes. In some embodiments, this can enable toxic intermediate assemblies and/or keep the growth rate of cells high during outgrowth steps and until the circuit is ready for final operation.

Aspects of the invention relate to kits, including kits comprising a BioFPGA or a BioPLA. In some embodiments, a kit comprises a cell or a bacterial strain comprising a reconfigurable chromosome. In other embodiments, a kit comprises a plasmid containing a BioFPGA or a BioPLA. In some embodiments, a kit comprises one or more plasmids for recombination with the BioFPGA or BioPLA, such as a library of plasmids in the appropriate format, with dynamically addressible attachment sites, while in other embodiments, one or more plasmids are not contained within the kit but, rather, are provided separately. In some embodiments, a kit further comprises one or more oligonucleotides for conducting MAGE. In some embodiments, the kit includes sets of oligonucleotides (ssDNA) predesigned to allow addressing of att sites to specific overlapping regions. In some embodiments, a kit comprises further components such as one or more buffers or reagents and/or instructions for use of the BioFPGA such as, for example, instructions for conducting MAGE and/or for conducting recombination.

It should be appreciated that the methods described herein encompass the use of any type of cell. The cell can be a eukaryotic or prokaryotic cell. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*.

In some embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. In certain embodiments, the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, a plant cell, an insect cell or a mammalian cell. In certain embodiments, the mammalian cell is a human cell.

The BioFPGA and BioPLAs described herein offer a valuable alternative to existing approaches to nucleic acid assembly. BioFPGAs and BioPLAs support rapid prototyping of new biocircuits without the need for in vitro DNA assembly, while simultaneously incorporating useful parts constructed by other means into its library of choices for the end user. BioFPGAs and BioPLAs represent significant opportunities for industries looking to rapidly explore different circuit configurations to optimize a biological process. The approaches described herein also enable organizations with lower in-house biology skills, for example in the energy sector, to adopt synthetic biology approaches. Approaches described herein represent a general class of architectures raising the level of programmability and abstraction for complex biosystem design.

EXAMPLES

Example 1

Bio-Field Programmable Array

Recombineering Protocol

Methods were adapted from Moserg et al. (2010) "Lambda Red Recombineering in *Escherichia coli* Occurs Through a Fully Single-Stranded Intermediate." *Genetics* 186(3):791-9 and Wang et al. (2009), "Programming cells by multiplex genome engineering and accelerated evolution." *Nature* 460(7257):894-8.

Generation of Insert

An insertion cassette for integration into the *E. coli* chromosome was produced by PCR amplifying the BioBrick J85221 in plasmid pSB1A2 with primers that encoded 45 base pairs of the lacZ gene on either end of the cassette. The 45 base pair sequences were the same as those used by Mosberg et al.

The two primers were as follows, where capital letters correspond to sequence of lacZ and lower case letters correspond to the primer sequence that binds to J85221 for amplification.

```
lacZ::BioBrick forward
                                        (SEQ ID NO: 14)
5'- TGACCATGATTACGGATTCACTGGCCGTCGTTTTACAACGTCGTG

gaattcgcggccgcttctag -3'

lacZ::BioBrick reverse
                                        (SEQ ID NO: 15)
5'- GTGCTGCAAGGCGATTAAGTTGGGTAACGCCAGGGTTTTCCCAGT

ctgcagcggccgctactagt -3'
```

The PCR was conducted with Pfx Supermix (Invitrogen, Carlsbad, Calif.). Approximately 2 ng of plasmid template was used, and primers were added at 0.4 uM. The PCR program was: 94° C. (1 minute); 30 cycles of 94° C. (30 seconds), 63° C. (30 seconds), 68° C. (2 minutes and 15 seconds); 68° C. (10 minutes). In order to degrade plasmid template DNA, 1 μl of DpnI (New England Biolabs, Ipswich, Mass.) was added to the PCR reaction and the new reaction was incubated for 1.5 hours at 37° C. The insert was purified with a gel purification kit (Qiagen, Valencia, Calif.) after running on an electrophoresis gel for 30 minutes (1% agarose, 125 V).

Transforming Cells

Strain EcNR2 (NmutS::cat N(ybhB-bioAB)::[λcI857 N(croea59)::tetR-bla]), as described in Wang, et. al., was used to integrate the insertion cassette into the chromosome. A 3 mL culture in LB media supplemented with ampicillin (100 μg/mL) was inoculated from a single colony of EcNR2 and grown overnight. This culture was diluted 100× into a 3 mL culture of LB supplemented with ampicillin (100 μg/mL). This culture was grown until it reached an OD (optical density) of 0.5, at which point it was induced for recombination functions by placing it in a 42° C. heat bath for 15 minutes while shaking. The culture was then chilled in an ice-water slurry for 15 minutes. A 1 mL aliquot was removed and spun down to a pellet before the supernatant was removed, and the pellet was resuspended in cold water. This washing process was repeated twice before the pellet was suspended in 50 μL of water containing 50-150 ng of insert DNA.

This 50 μL aliquot was then transferred to a precooled 1 mm electroporation cuvette (Bio-rad) and electroporated at 1.8 kV before being resuspended in 3 mL LB and outgrown for three hours shaking at 30° C. 1 mL of outgrowth culture was spun down and resuspended in 100 μL of water to be plates on LB agar plates with kanamycin (25 μg/ml). To check for transformation efficiency, 100 μL of a $1\times10^{-4}$ dilution of the outgrowth culture was plates on LB agar plates with ampicillin (100 μg/ml). Transformation efficiency was determined by the number of transformed cells relative to the total number of viable cells (accounting for plating volume and dilution).

Example 2

Configuration and Recombination Using a Bio-FPGA

Use of a Bio-FPGA can involve two steps: configuration, such as by the use of MAGE, and recombination, such as recombination between a plasmid and a Bio-FPGA that is located on a chromosome such as a bacterial chromosome.

Configuration by MAGE

Methods for conducting MAGE were adapted from Wang et al. (2009), "Programming cells by multiplex genome engineering and accelerated evolution." *Nature* 460(7257): 894-8. The oligonucleotide cat_fwd_restore (below) was transformed into strain EcFI5 to mutate a defective chloramphenicol resistance gene into its functional sequence by turning off of an upstream stop codon (see Wang et al.).

```
cat_fwd_restore:
                                        (SEQ ID NO: 37)
5'GCATCGTAAAGAACATTTTGAGGCATTTCAGTCAGTTGCTCAATGTAC

CTATAACCAGACCGTTCAGCTGGATATTACGGCCTTTTTAAA -3'
```

Strain EcFI5 as described in Wang, et. al., was used to integrate the insertion cassette into the chromosome. A 3 mL culture in LB media supplemented with ampicillin (100 μg/mL) was inoculated from a single colony of EcFI5 and grown overnight. This culture was diluted 100× into a 30 mL culture of LB supplemented with ampicillin (100 μg/mL). This culture was grown until it reached an OD (optical density) of 0.5, at which point it was induced for recombination functions by placing it in a 42° C. heat bath for 15 minutes while shaking. The culture was then chilled in an ice-water slurry for 15 minutes. A 1 mL aliquot was removed and spun down to a pellet before the supernant was removed, and the pellet was resuspended in cold water. This washing process was repeated twice before the pellet was suspended in a 45 μL solution of 0.5 μM cat_fwd_restore.

This resuspended cell and oligo mixture was then transferred to a precooled 1 mm electroporation cuvette (Bio-rad, Hercules, Calif.) and electroporated at 1.8 kV before being resuspended in 1 mL LB and outgrown for two hours shaking at 30° C.

To select for the desired mutation, 20 μL of the outgrowth culture was plated on LB agar with chloramphenicol (25 μg/ml). To check for mutation efficiency, 20 μL of the outgrowth culture was plated on LB agar plates with ampicillin (100 μg/ml) and efficiency was determined by the number of transformed colonies (on the chloramphenicol plate) relative to the total number of viable colonies (on the ampicillin plate).

Configuration and Recombination

A self integrating plasmid (pLibary1) containing one or more source library parts is provided along with an *E.coli* strain which contains the BioFPGA chassis target sites (BFa1), which is constructed, for example, with pTet as the inducible promoter (inducible with aTc, anhydrous tetracycline). The user selects the first library part and integrates it into the second target site.

Steps include:

1. Transform BF1 via pLibraryl
   a. (optional: select with Kanamycin)
2. Use MAGE protocol to transform BF1 via electroporation with the four addressing oligos.
   a. Note this step may be combined with step 1
3. Use IPTG to induce recombination
4. Use aTc to induce counterselection markers
5. Verify results Four representative examples of addressing oligonucleotides to recombine source part 1 into target site 2 are: (The * shows a phosphorothioate bond)

```
Oligo1:Ab(3):B:O(1):P'=
                                        (SEQ ID NO: 44)
G*A*CTTAAGAGTCTATCACCCCTAGGGCCCTTTCCCGGATATAAACGCC

AGGTTGAATCCGCATTTcctgctttATTATACtaagttgg*c*a

Oligo2:P:O(2):B':Ab(4)=
                                        (SEQ ID NO: 45)
t*c*agctttCTTATACtaacttgagcGGAGCTACGATGGATGAGTCTGG

GTGGAGCGCGCCCCATTTATACCGTGAGTAGGGTCGACCA*A*G

Oligo3:P:O(1):B':Ap(1)=
                                        (SEQ ID NO: 46)
t*c*agctttATTATACtaacttgagcAACCGCAAGATGCGTCGGTGTAC

AAATAATTGTCAACAGACCGTCGTGTTTTGAAAATGGTAC*C*A

Oligo4:Ap(2):B:O(2):P'=
                                        (SEQ ID NO: 47)
G*C*ATCTTCGGGCGGTCTCAATCAAGCATGGATTACGGTGTTTACTCTG

TCCTGCGGTTACCCATGcctgctttCTTATACtaagttgg*c*a
```

Method for Performing Steps 1 and 2 Above:

A strain such as BFa1 is used, containing a BioFPGA chasiss with aTc inducible counterselection, and suitable for MAGE (lambda red, recA+, mutS−). A 3 mL culture in LB media supplemented with ampicillin (100 μg/mL) is inoculated from a single colony of BFa1 and grown overnight. This culture is diluted 100× into a 30 mL culture of LB supplemented with ampicillin (100 μg/mL). This culture is grown until reaching an OD (optical density) of 0.5, at which point it is induced for recombination functions by placing it in a 42° C. heat bath for 15 minutes while shaking. The culture is chilled in an ice-water slurry for 15 minutes. A 1 mL aliquot is removed and spun down to a pellet before the supernatant was removed, and the pellet is resuspended in cold water. This washing process is repeated twice before the pellet is suspended in a 45 μL solution of 0.125 μM of each of the four addressing Oligo1, Oligo2, Oligo3, Oligo4 and 1-5ng of plasmid pLibrary1.

The resuspended cell and oligo/plasmid mixture is transferred to a precooled 1 mm electroporation cuvette (Bio-rad) and electroporated at 1.8 kV before being resuspended in 1 mL LB and outgrown for two hours shaking at 30° C.

After outgrowth, the cells are induced with 0.5 mM of IPTG for 1 or more hours to induce recombination. To induce counterselection, the cells are further induced with 200ng/m1 aTc for 2-6 hours. The exact concentration and duration of induction can be adjusted experimentally to maximize efficiency. To check mutation and recombination efficiency, 20 μl of uninduced outgrowth culture can be plated on LB agar plates with ampicillin (100 μg/ml) and compared to 20 μl of induced outgrowth culture (also on LB agar plates with ampicillin (100 μg/ml)). Efficiency may be determined by the number of mutated and recombined colonies (on the induced plate) relative to the total number of viable colonies (the uninduced plate).

Example 3

Bio-Programmable Logic Array

Unlike the BioFPGA, the BioPLA protocol does not involve an input library or recombination. A user of the BioPLA begins with a cell such as a supplied *E.coli* strain which contains the BioPLA chassis (BPLA1), which is constructed using standard cloning and recombineering protocols. In this example, the user will configure BPLA1 (see figure PLA in description), to compute the following function:

Green (GFP) phenotype when IPTG is present.

Blue (LacZ) phenotype when both aTc and AHL are present (independent of IPTG).

No AHL output (LuxI protein will be unexpressed).

The MAGE protocol is used, with the following oligos: (note: in this example, the assumption is that the initial state of the BPLA1 strain is with all configuration bits off. That is, genes will have stop codons inserted and the pLac+pLux+pCI promoters will be off.)

Oligo1: mutates first pLac+pLux+pCI to function as pLac only

Oligo2: restore first GFP gene

Oligo3: mutates second pLac+pLux+pCI to function as pLux+PCI

Oligo4: restore second LacZ gene

The circuit is tested and operated by inducing with combinations of IPTG, aTc, and AHL and testing for the appropriate output.

An example oligo for restoring GFP in part J85201 is:

```
                                            (SEQ ID NO: 48)
g*a*gaagaacttttcactggagttgtcccaattcttgttgaattagatg

gtgatgttaatgggcacaaattttctgtcagtggagagggg*t*g
```

(J85201 sequence with added stop codon:

```
                                            (SEQ ID NO: 49)
aaagaggagaaatactagatgcgtaaaggagaagaacttttcactggagt

tgtcccaattcttgttgaattagatggtgatgttaatgggcacaaatttt

ctgacagtggagagggtgaaggtgatgcaacatacggaaaacttaccctt

aaatttatttgcactactggaaaactacctgttccatggccaacacttgt

cactactttcggttatggtgttcaatgctttgcgagatacccagatcata

tgaaacagcatgactttttcaagagtgccatgcccgaaggttatgtacag

gaaagaactatatttttcaaagatgacgggaactacaagacacgtgctga

agtcaagtttgaaggtgatacccttgttaatagaatcgagttaaaaggta

ttgattttaaagaagatggaaacattcttggacacaaattggaatacaac
```

-continued

```
tataactcacacaatgtatacatcatggcagacaaacaaaagaatggaat

caaagttaacttcaaaattagacacaacattgaagatggaagcgttcaac

tagcagaccattatcaacaaaatactccaattggcgatggccctgtcctt

ttaccagacaaccattacctgtccacacaatctgccctttcgaaagatcc

caacgaaaagagagaccacatggtccttcttgagtttgtaacagctgctg

ggattacacatggcatggatgaactatacaaataataa)
```

An example oligo for restoring the LacZ gene is:

```
cat_restore76thio4:
                                            (SEQ ID NO: 20)
T*G*GATATACCACCGTTGATATATCCCAATGGCATCGTAAAGAACATTT

TGAGGCATTTCAGTCAGTTGCTCAATGTACCTATAACCAG*A*C
```

Oligos for modifying promoter repressors and operon sites are more complex, but similarly constructed. Single or few by mutations which 'break' each activator or operator site can be restored. In rare cases, if more than 20 bp mutations are required, then multiple MAGE oligos are used for that target.

Example restored pLux/CI

```
>BBa_K415032 Part-only sequence (68 bp)
                                            (SEQ ID NO: 50)
acctgtaggatcgtacaggtttacgcaagaaaatggtttgttatagtcga

atacctctggcggtgata
```

Example restored pLac

```
>BBa_R0011 Part-only sequence (55 bp)
                                            (SEQ ID NO: 51)
Aattgtgagcggataacaattgacattgtgagcggataacaagatactga

gcaca
```

Note: In some embodiments, the full 90mer depends on the surrounding sequence in the BioPLA and can include addressing variations so that the three (in this case) promoter instances in the BioPLA can be targeted individually.

Some other example of restored promoter sequences from the BioBricks parts registry are: Example PCI

```
>BBa_R0052 Part-only sequence (46 bp)
                                            (SEQ ID NO: 52)
Ttgacaaacaagatacattgtatgaaaatacaagaaagtttgttga
```

Example restored pLux

```
>BBa_R0062 Part-only sequence (55 bp)
                                            (SEQ ID NO: 53)
Acctgtaggatcgtacaggtttacgcaagaaaatggtttgttatagtcga

ataaa
```

Example Plac/CI

```
>BBa_K101001 Part-only sequence (116 bp)
                                            (SEQ ID NO: 54)
Gcgcaacgcaattaatgtgagttagctcactcattaggcataacaccgtg

cgtgttgactattttacctctggcggtgataatgtgtggaattgtgagcg

gataaaattcacaca
```

Example restored PLux/pLac

>BBa_I751502 Part-only sequence (74 bp)

(SEQ ID NO: 55)

Acctgtaggatcgtacaggtttacttgtgagcggataacaatatagtgtg tggaattgtgagcggataacaatt

Further Sequences Associated with Examples 1 and 2

The following sequences are available through the BioBricks database:

J85201-RBS (Elowitz 1999) + green fluorescent protein derived from jellyfish *Aequeora victoria* wild-type GFP:

(SEQ ID NO: 1)

aaagaggagaaatactagatgcgtaaaggagaagaacttttcactggagt tgtcccaattcttgttgaattagatggtgatgttaatgggcacaaatttt ctgtcagtggagagggtgaaggtgatgcaacatacggaaaacttaccctt aaatttatttgcactactggaaaactacctgttccatggccaacacttgt cactactttcggttatggtgttcaatgctttgcgagatacccagatcata tgaaacagcatgactttttcaagagtgccatgcccgaaggttatgtacag gaaagaactatatttttcaaagatgacgggaactacaagacacgtgctga agtcaagtttgaaggtgatacccttgttaatagaatcgagttaaaaggta ttgattttaaagaagatggaaacattcttggacacaaattggaatacaac tataactcacacaatgtatacatcatggcagacaaacaaaagaatggaat caaagttaacttcaaaattagacacaacattgaagatggaagcgttcaac tagcagaccattatcaacaaaatactccaattggcgatggccctgtcctt ttaccagacaaccattacctgtccacacaatctgccctttcgaaagatcc caacgaaaagagagaccacatggtccttcttgagtttgtaacagctgctg ggattacacatggcatggatgaactatacaaataataa J85202- TetR repressible promoter + RBS (Elowitz 1999) + green fluorescent protein derived from jellyfish *Aequeora victoria* wild-type GFP:

(SEQ ID NO: 2)

tccctatcagtgatagagattgacatccctatcagtgatagagatactga gcactactagagaaagaggagaaatactagatgcgtaaaggagaagaact tttcactggagttgtcccaattcttgttgaattagatggtgatgttaatg ggcacaaattttctgtcagtggagagggtgaaggtgatgcaacatacgga aaacttacccttaaatttatttgcactactggaaaactacctgttccatg gccaacacttgtcactactttcggttatggtgttcaatgctttgcgagat acccagatcatatgaaacagcatgactttttcaagagtgccatgcccgaa ggttatgtacaggaaagaactatatttttcaaagatgacgggaactacaa gacacgtgctgaagtcaagtttgaaggtgatacccttgttaatagaatcg agttaaaaggtattgattttaaagaagatggaaacattcttggacacaaa ttggaatacaactataactcacacaatgtatacatcatggcagacaaaca aaagaatggaatcaaagttaacttcaaaattagacacaacattgaagatg gaagcgttcaactagcagaccattatcaacaaaatactccaattggcgat ggccctgtccttttaccagacaaccattacctgtccacacaatctgccct -continued ttcgaaagatcccaacgaaaagagagaccacatggtccttcttgagtttg taacagctgctgggattacacatggcatggatgaactatacaaataataa J85203- Composite part to detect 3OC6HSL and produce a red fluorescent protein and TetR:

(SEQ ID NO: 3)

tggtgcaaaacctttcgcggtatggcatgatagcgcctactagagaaaga ggagaaatactagatgaaaaacataaatgccgacgacacatacagaataa ttaataaaattaaagcttgtagaagcaataatgatattaatcaatgctta tctgatatgactaaaatggtacattgtgaatattatttactcgcgatcat ttatcctcattctatggttaaatctgatatttcaatcctagataattacc ctaaaaaatggaggcaatattatgatgacgctaatttaataaaatatgat cctatagtagattattctaactccaatcattcaccaattaattggaatat atttgaaaacaatgctgtaaataaaaaatctccaaatgtaattaaagaag cgaaaacatcaggtcttatcactgggtttagtttccctattcatacggct aacaatggcttcggaatgcttagttttgcacattcagaaaaagacaacta tatagatagtttatttttacatgcgtgtatgaacataccattaattgttc cttctctagttgataattatcgaaaaataaatatagcaaataataaatca aacaacgatttaaccaaaagagaaaaagaatgtttagcgtgggcatgcga aggaaaaagctcttgggatatttcaaaaatattaggttgcagtgagcgta ctgtcactttccatttaaccaatgcgcaaatgaaactcaatacaacaaac cgctgccaaagtatttctaaagcaattttaacaggagcaattgattgccc atactttaaaaattaataacactgatagtgctagtgtagatcactactag agccaggcatcaaataaaacgaaaggctcagtcgaaagactgggcctttc gttttatctgttgtttgtcggtgaacgctctctactagagtcacactggc tcaccttcgggtgggcctttctgcgtttatatactagagacctgtaggat cgtacaggtttacgcaagaaaatggtttgttatagtcgaataaatactag agaaagaggagaaatactagatggcttcctccgaagacgttatcaaagag ttcatgcgtttcaaagttcgtatggaaggttccgttaacggtcacgagtt cgaaatcgaaggtgaaggtgaaggtcgtccgtacgaaggtacccagaccg ctaaactgaaagttaccaaaggtggtccgctgccgttcgcttgggacatc ctgtccccgcagttccagtacggttccaaagcttacgttaaacacccggc tgacatcccggactacctgaaactgtccttcccggaaggtttcaaatggg aacgtgttatgaacttcgaagacggtggtgttgttaccgttacccaggac tcctccctgcaagacggtgagttcatctacaaagttaaactgcgtggtac caacttcccgtccgacggtccggttatgcagaaaaaaaccatgggttggg aagcttccaccgaacgtatgtacccggaagacggtgctctgaaaggtgaa atcaaaatgcgtctgaaactgaaagacggtggtcactacgacgctgaagt taaaaccacctacatggctaaaaaaccggttcagctgccgggtgcttaca aaaccgacatcaaactggacatcacctcccacaacgaagactacaccatc gttgaacagtacgaacgtgctgaaggtcgtcactccaccggtgcttaata acgctgatagtgctagtgtagatcgctactagagaaagaggagaaatact agatgtccagattagataaaagtaaagtgattaacagcgcattagagctg -continued cttaatgaggtcggaatcgaaggtttaacaacccgtaaactcgcccagaa gctaggtgtagagcagcctacattgtattggcatgtaaaaaataagcggg ctttgctcgacgccttagccattgagatgttagataggcaccatactcac ttttgccctttagaaggggaaagctggcaagattttttacgtaataacgc taaaagttttagatgtgctttactaagtcatcgcgatggagcaaaagtac atttaggtacacggcctacagaaaaacagtatgaaactctcgaaaatcaa ttagcctttttatgccaacaaggtttttcactagagaatgcattatatgc actcagcgctgtggggcattttactttaggttgcgtattggaagatcaag agcatcaagtcgctaaagaagaaagggaaacacctactactgatagtatg ccgccattattacgacaagctatcgaattatttgatcaccaaggtgcaga gccagccttcttattcggccttgaattgatcatatgcggattagaaaaac aacttaaatgtgaaagtgggtccgctgcaaacgacgaaaactacgcttta gtagcttaataacactgatagtgctagtgtagatcactactagagccagg catcaaataaaacgaaaggctcagtcgaaagactgggcctttcgttttat ctgttgtttgtcggtgaacgctctctactagagtcacactggctcacctt cgggtgggcctttctgcgtttata J85204- Composite part to detect 3OC6HSL and produce RFP, or in the absence of 3OC6HSL to produce GFP. Uses TetR/Ptet regulatory mechanism:

(SEQ ID NO: 4)

tggtgcaaaacctttcgcggtatggcatgatagcgcctactagagaaaga ggagaaatactagatgaaaaacataaatgccgacgacacatacagaataa ttaataaaattaaagcttgtagaagcaataatgatattaatcaatgctta tctgatatgactaaaatggtacattgtgaatattatttactcgcgatcat ttatcctcattctatggttaaatctgatatttcaatcctagataattacc ctaaaaaatggaggcaatattatgatgacgctaatttaataaaatatgat cctatagtagattattctaactccaatcattcaccaattaattggaatat atttgaaaacaatgctgtaaataaaaaatctccaaatgtaattaaagaag cgaaaacatcaggtcttatcactgggtttagtttccctattcatacggct aacaatggcttcggaatgcttagttttgcacattcagaaaaagacaacta tatagatagtttatttttacatgcgtgtatgaacataccattaattgttc cttctctagttgataattatcgaaaaataaatatagcaaataataaatca aacaacgatttaaccaaaagagaaaaagaatgtttagcgtgggcatgcga aggaaaaagctcttgggatatttcaaaaatattaggttgcagtgagcgta ctgtcactttccatttaaccaatgcgcaaatgaaactcaatacaacaaac cgctgccaaagtatttctaaagcaattttaacaggagcaattgattgccc atactttaaaaattaataacactgatagtgctagtgtagatcactactag agccaggcatcaaataaaacgaaaggctcagtcgaaagactgggcctttc gttttatctgttgtttgtcggtgaacgctctctactagagtcacactggc tcaccttcgggtgggcctttctgcgtttatatactagagacctgtaggat cgtacaggtttacgcaagaaaatggtttgttatagtcgaataaatactag agaaagaggagaaatactagatggcttcctccgaagacgttatcaaagag -continued ttcatgcgtttcaaagttcgtatggaaggttccgttaacggtcacgagtt cgaaatcgaaggtgaaggtgaaggtcgtccgtacgaaggtacccagaccg ctaaactgaaagttaccaaaggtggtccgctgccgttcgcttgggacatc ctgtccccgcagttccagtacggttccaaagcttacgttaaacacccggc tgacatcccggactacctgaaactgtccttcccggaaggtttcaaatggg aacgtgttatgaacttcgaagacggtggtgttgttaccgttacccaggac tcctccctgcaagacggtgagttcatctacaaagttaaactgcgtggtac caacttcccgtccgacggtccggttatgcagaaaaaaaccatgggttggg aagcttccaccgaacgtatgtacccggaagacggtgctctgaaaggtgaa atcaaaatgcgtctgaaactgaaagacggtggtcactacgacgctgaagt taaaaccacctacatggctaaaaaaccggttcagctgccgggtgcttaca aaaccgacatcaaactggacatcacctcccacaacgaagactacaccatc gttgaacagtacgaacgtgctgaaggtcgtcactccaccggtgcttaata acgctgatagtgctagtgtagatcgctactagagaaagaggagaaatact agatgtccagattagataaaagtaaagtgattaacagcgcattagagctg cttaatgaggtcggaatcgaaggtttaacaacccgtaaactcgcccagaa gctaggtgtagagcagcctacattgtattggcatgtaaaaaataagcggg ctttgctcgacgccttagccattgagatgttagataggcaccatactcac ttttgccctttagaaggggaaagctggcaagattttttacgtaataacgc taaaagttttagatgtgctttactaagtcatcgcgatggagcaaaagtac atttaggtacacggcctacagaaaaacagtatgaaactctcgaaaatcaa ttagcctttttatgccaacaaggtttttcactagagaatgcattatatgc actcagcgctgtggggcattttactttaggttgcgtattggaagatcaag agcatcaagtcgctaaagaagaaagggaaacacctactactgatagtatg ccgccattattacgacaagctatcgaattatttgatcaccaaggtgcaga gccagccttcttattcggccttgaattgatcatatgcggattagaaaaac aacttaaatgtgaaagtgggtccgctgcaaacgacgaaaactacgcttta gtagcttaataacactgatagtgctagtgtagatcactactagagccagg catcaaataaaacgaaaggctcagtcgaaagactgggcctttcgttttat ctgttgtttgtcggtgaacgctctctactagagtcacactggctcacctt cgggtgggcctttctgcgtttatatactagagtccctatcagtgatagag attgacatccctatcagtgatagagatactgagcactactagagaaagag gagaaatactagatgcgtaaaggagaagaacttttcactggagttgtccc aattcttgttgaattagatggtgatgttaatgggcacaaattttctgtca gtggagagggtgaaggtgatgcaacatacggaaaacttacccttaaattt atttgcactactggaaaactacctgttccatggccaacacttgtcactac tttcggttatggtgttcaatgctttgcgagatacccagatcatatgaaac agcatgactttttcaagagtgccatgcccgaaggttatgtacaggaaaga actatatttttcaaagatgacgggaactacaagacacgtgctgaagtcaa gtttgaaggtgatacccttgttaatagaatcgagttaaaaggtattgatt ttaaagaagatggaaacattcttggacacaaattggaatacaactataac -continued tcacacaatgtatacatcatggcagacaaacaaaagaatggaatcaaagt taacttcaaaattagacacaacattgaagatggaagcgttcaactagcag accattatcaacaaaatactccaattggcgatggccctgtccttttacca gacaaccattacctgtccacacaatctgccctttcgaaagatcccaacga aaagagagaccacatggtccttcttgagtttgtaacagctgctgggatta cacatggcatggatgaactatacaaataataa J85205- Composite part to detect 3OC6HSL and produce a RFP, or in the absence of 3OC6HSL to produce GFP. Uses TetR/Ptet regulatory mechanism (alternative construction of J85204):

(SEQ ID NO: 5)

tggtgcaaaacctttcgcggtatggcatgatagcgcctactagagaaaga ggagaaatactagatgaaaaacataaatgccgacgacacatacagaataa ttaataaaattaaagcttgtagaagcaataatgatattaatcaatgctta tctgatatgactaaaatggtacattgtgaatattatttactcgcgatcat ttatcctcattctatggttaaatctgatatttcaatcctagataattacc ctaaaaaatggaggcaatattatgatgacgctaatttaataaaatatgat cctatagtagattattctaactccaatcattcaccaattaattggaatat atttgaaaacaatgctgtaaataaaaaatctccaaatgtaattaaagaag cgaaaacatcaggtcttatcactgggtttagtttccctattcatacggct aacaatggcttcggaatgcttagttttgcacattcagaaaaagacaacta tatagatagtttattttttacatgcgtgtatgaacataccattaattgttc cttctctagttgataattatcgaaaaataaatatagcaaataataaatca aacaacgatttaaccaaaagagaaaaagaatgtttagcgtgggcatgcga aggaaaaagctcttgggatatttcaaaaatattaggttgcagtgagcgta ctgtcactttccatttaaccaatgcgcaaatgaaactcaatacaacaaac cgctgccaaagtatttctaaagcaattttaacaggagcaattgattgccc atactttaaaaattaataacactgatagtgctagtgtagatcactactag agccaggcatcaaataaaacgaaaggctcagtcgaaagactgggcctttc gttttatctgttgtttgtcggtgaacgctctctactagagtcacactggc tcaccttcgggtgggcctttctgcgtttatatactagagacctgtaggat cgtacaggtttacgcaagaaaatggtttgttatagtcgaataaatactag agaaagaggagaaatactagatggcttcctccgaagacgttatcaaagag ttcatgcgtttcaaagttcgtatggaaggttccgttaacggtcacgagtt cgaaatcgaaggtgaaggtgaaggtcgtccgtacgaaggtacccagaccg ctaaactgaaagttaccaaaggtggtccgctgccgttcgcttgggacatc ctgtccccgcagttccagtacggttccaaagcttacgttaaacacccggc tgacatcccggactacctgaaactgtccttcccggaaggtttcaaatggg aacgtgttatgaacttcgaagacggtggtgttgttaccgttacccaggac tcctccctgcaagacggtgagttcatctacaaagttaaactgcgtggtac caacttcccgtccgacggtccggttatgcagaaaaaaaccatgggttggg aagcttccaccgaacgtatgtacccggaagacggtgctctgaaaggtgaa atcaaaatgcgtctgaaactgaaagacggtggtcactacgacgctgaagt -continued taaaaccacctacatggctaaaaaaccggttcagctgccgggtgcttaca aaaccgacatcaaactggacatcacctcccacaacgaagactacaccatc gttgaacagtacgaacgtgctgaaggtcgtcactccaccggtgcttaata acgctgatagtgctagtgtagatcgctactagagaaagaggagaaatact agatgtccagattagataaaagtaaagtgattaacagcgcattagagctg cttaatgaggtcggaatcgaaggtttaacaacccgtaaactcgcccagaa gctaggtgtagagcagcctacattgtattggcatgtaaaaaataagcggg ctttgctcgacgccttagccattgagatgttagataggcaccatactcac ttttgccctttagaaggggaaagctggcaagatttttttacgtaataacgc taaaagttttagatgtgctttactaagtcatcgcgatggagcaaaagtac atttaggtacacggcctacagaaaaacagtatgaaactctcgaaaatcaa ttagcctttttatgccaacaaggtttttcactagagaatgcattatatgc actcagcgctgtggggcattttactttaggttgcgtattggaagatcaag agcatcaagtcgctaaagaagaaagggaaacacctactactgatagtatg ccgccattattacgacaagctatcgaattatttgatcaccaaggtgcaga gccagccttcttattcggccttgaattgatcatatgcggattagaaaaac aacttaaatgtgaaagtgggtccgctgcaaacgacgaaaactacgcttta gtagcttaataacactgatagtgctagtgtagatcactactagagccagg catcaaataaaacgaaaggctcagtcgaaagactgggcctttcgttttat ctgttgtttgtcggtgaacgctctctactagagtcacactggctcacctt cgggtgggcctttctgcgtttatatactagagtccctatcagtgatagag attgacatccctatcagtgatagagatactgagcactactagagaaagag gagaaatactagatgcgtaaaggagaagaacttttcactggagttgtccc aattcttgttgaattagatggtgatgttaatgggcacaaattttctgtca gtggagagggtgaaggtgatgcaacatacggaaaacttacccttaaattt atttgcactactggaaaactacctgttccatggccaacacttgtcactac tttcggttatggtgttcaatgctttgcgagatacccagatcatatgaaac agcatgactttttcaagagtgccatgcccgaaggttatgtacaggaaaga actatatttttcaaagatgacgggaactacaagacacgtgctgaagtcaa gtttgaaggtgatacccttgttaatagaatcgagttaaaaggtattgatt ttaaagaagatggaaacattcttggacacaaattggaatacaactataac tcacacaatgtatacatcatggcagacaaacaaaagaatggaatcaaagt taacttcaaaattagacacaacattgaagatggaagcgttcaactagcag accattatcaacaaaatactccaattggcgatggccctgtcctttacca gacaaccattacctgtccacacaatctgccctttcgaaagatcccaacga aaagagagaccacatggtccttcttgagtttgtaacagctgctgggatta cacatggcatggatgaactatacaaataataatactagagccaggcatca aataaaacgaaaggctcagtcgaaagactgggcctttcgttttatctgtt gtttgtcggtgaacgctctctactagagtcacactggctcaccttcgggt gggcctttctgcgtttata -continued J85206- RBS + Tet(A):

(SEQ ID NO: 6)

aaagaggagaaatactagatgaaatctaacaatgcgctcatcgtcatcct
cggcaccgtcaccctggatgctgtaggcataggcttggttatgccggtac
tgccgggcctcttgcgggatatcgtccattccgacagcatcgccagtcac
tatggcgtgctgctagcgctatatgcgttgatgcaatttctatgcgcacc
cgttctcggagcactgtccgaccgctttggccgccgcccagtcctgctcg
cttcgctacttggagccactatcgactacgcgatcatggcgaccacaccc
gtcctgtggatcctctacgccggacgcatcgtggccggcatcaccggcgc
cacaggtgcggttgctggcgcctatatcgccgacatcaccgatggggaag
atcgggctcgccacttcgggctcatgagcgcttgtttcggcgtgggtatg
gtggcaggccccgtggccgggggactgttgggcgccatctccttgcatgc
accattccttgcggcggcggtgctcaacggcctcaacctactactgggct
gcttcctaatgcaggagtcgcataagggagagcgtcgaccgatgcccttg
agagccttcaacccagtcagctccttccggtgggcgcggggcatgactat
cgtcgccgcacttatgactgtcttctttatcatgcaactcgtaggacagg
tgccggcagcgctctgggtcattttcggcgaggaccgctttcgctggagc
gcgacgatgatcggcctgtcgcttgcggtattcggaatcttgcacgccct
cgctcaagccttcgtcactggccccgccaccaaacgtttcggcgagaagc
aggccattatcgccggcatggcggccgacgcgctgggctacgtcttgctg
gcgttcgcgacgcgaggctggatggccttccccattatgattcttctcgc
ttccggcggcatcgggatgcccgcgttgcaggccatgctgtccaggcagg
tagatgacgaccatcagggacagcttcaaggatcgctcgcggctcttacc
agcctaacttcgatcattggaccgctgatcgtcacggcgatttatgccgc
ctcggcgagcacatggaacgggttggcatggattgtaggcgccgccctat
accttgtctgcctccccgcgttgcgtcgcggtgcatggagccgggccacc
tcgacctaa J85207- GFP marker and tetracycline resistance to be used in a chromosomal integration test:

(SEQ ID NO: 7)

tccctatcagtgatagagattgacatccctatcagtgatagagatactga
gcactactagagaaagaggagaaatactagatgcgtaaaggagaagaact
tttcactggagttgtcccaattcttgttgaattagatggtgatgttaatg
ggcacaaattttctgtcagtggagagggtgaaggtgatgcaacatacgga
aaacttacccttaaatttatttgcactactggaaaactacctgttccatg
gccaacacttgtcactactttcggttatggtgttcaatgctttgcgagat
acccagatcatatgaaacagcatgactttttcaagagtgccatgcccgaa
ggttatgtacaggaaagaactatatttttcaaagatgacgggaactacaa
gacacgtgctgaagtcaagtttgaaggtgatacccttgttaatagaatcg
agttaaaaggtattgattttaaagaagatggaaacattcttggacacaaa
ttggaatacaactataactcacacaatgtatacatcatggcagacaaaca
aaagaatggaatcaaagttaacttcaaaattagacacaacattgaagatg
gaagcgttcaactagcagaccattatcaacaaaatactccaattggcgat -continued ggccctgtccttttaccagacaaccattacctgtccacacaatctgccct
ttcgaaagatcccaacgaaaagagagaccacatggtccttcttgagtttg
taacagctgctgggattacacatggcatggatgaactatacaaataataa
tactagagaaagaggagaaatactagatgaaatctaacaatgcgctcatc
gtcatcctcggcaccgtcaccctggatgctgtaggcataggcttggttat
gccggtactgccgggcctcttgcgggatatcgtccattccgacagcatcg
ccagtcactatggcgtgctgctagcgctatatgcgttgatgcaatttcta
tgcgcacccgttctcggagcactgtccgaccgctttggccgccgcccagt
cctgctcgcttcgctacttggagccactatcgactacgcgatcatggcga
ccacacccgtcctgtggatcctctacgccggacgcatcgtggccggcatc
accggcgccacaggtgcggttgctggcgcctatatcgccgacatcaccga
tggggaagatcgggctcgccacttcgggctcatgagcgcttgtttcggcg
tgggtatggtggcaggccccgtggccgggggactgttgggcgccatctcc
ttgcatgcaccattccttgcggcggcggtgctcaacggcctcaacctact
actgggctgcttcctaatgcaggagtcgcataagggagagcgtcgaccga
tgcccttgagagccttcaacccagtcagctccttccggtgggcgcggggc
atgactatcgtcgccgcacttatgactgtcttctttatcatgcaactcgt
aggacaggtgccggcagcgctctgggtcattttcggcgaggaccgctttc
gctggagcgcgacgatgatcggcctgtcgcttgcggtattcggaatcttg
cacgccctcgctcaagccttcgtcactggccccgccaccaaacgtttcgg
cgagaagcaggccattatcgccggcatggcggccgacgcgctgggctacg
tcttgctggcgttcgcgacgcgaggctggatggccttccccattatgatt
cttctcgcttccggcggcatcgggatgcccgcgttgcaggccatgctgtc
caggcaggtagatgacgaccatcagggacagcttcaaggatcgctcgcgg
ctcttaccagcctaacttcgatcattggaccgctgatcgtcacggcgatt
tatgccgcctcggcgagcacatggaacgggttggcatggattgtaggcgc
cgccctataccttgtctgcctccccgcgttgcgtcgcggtgcatggagcc
gggccacctcgacctaa J85208- Composite part to detect 3OC6HSL and produce RFP, or in the absence of 3OC6HSL to produce GFP and tetracycline resistance. Uses TetR/Ptet regulatory mechanism. Based on J85204 (when tetracycline resistance is not repressed, can lead to slow growth):

(SEQ ID NO: 8)

tggtgcaaaacctttcgcggtatggcatgatagcgcctactagagaaaga
ggagaaatactagatgaaaaacataaatgccgacgacacatacagaataa
ttaataaaattaaagcttgtagaagcaataatgatattaatcaatgctta
tctgatatgactaaaatggtacattgtgaatattatttactcgcgatcat
ttatcctcattctatggttaaatctgatatttcaatcctagataattacc
ctaaaaaatggaggcaatattatgatgacgctaatttaataaaatatgat
cctatagtagattattctaactccaatcattcaccaattaattggaatat
atttgaaaacaatgctgtaaataaaaaatctccaaatgtaattaaagaag
cgaaaacatcaggtcttatcactgggtttagtttccctattcatacggct -continued aacaatggcttcggaatgcttagttttgcacattcagaaaaagacaacta tatagatagtttatttttacatgcgtgtatgaacataccattaattgttc cttctctagttgataattatcgaaaaataaatatagcaaataataaatca aacaacgatttaaccaaaagagaaaaagaatgtttagcgtgggcatgcga aggaaaaagctcttgggatatttcaaaaatattaggttgcagtgagcgta ctgtcactttccatttaaccaatgcgcaaatgaaactcaatacaacaaac cgctgccaaagtatttctaaagcaattttaacaggagcaattgattgccc atactttaaaaattaataacactgatagtgctagtgtagatcactactag agccaggcatcaaataaaacgaaaggctcagtcgaaagactgggcctttc gttttatctgttgtttgtcggtgaacgctctctactagagtcacactggc tcaccttcgggtgggcctttctgcgtttatatactagagacctgtaggat cgtacaggtttacgcaagaaaatggtttgttatagtcgaataaatactag agaaagaggagaaatactagatggcttcctccgaagacgttatcaaagag ttcatgcgtttcaaagttcgtatggaaggttccgttaacggtcacgagtt cgaaatcgaaggtgaaggtgaaggtcgtccgtacgaaggtacccagaccg ctaaactgaaagttaccaaaggtggtccgctgccgttcgcttgggacatc ctgtccccgcagttccagtacggttccaaagcttacgttaaacacccggc tgacatcccggactacctgaaactgtccttcccggaaggtttcaaatggg aacgtgttatgaacttcgaagacggtggtgttgttaccgttacccaggac tcctccctgcaagacggtgagttcatctacaaagttaaactgcgtggtac caacttcccgtccgacggtccggttatgcagaaaaaaaccatgggttggg aagcttccaccgaacgtatgtacccggaagacggtgctctgaaaggtgaa atcaaaatgcgtctgaaactgaaagacggtggtcactacgacgctgaagt taaaaccacctacatggctaaaaaaccggttcagctgccgggtgcttaca aaaccgacatcaaactggacatcacctcccacaacgaagactacaccatc gttgaacagtacgaacgtgctgaaggtcgtcactccaccggtgcttaata acgctgatagtgctagtgtagatcgctactagagaaagaggagaaatact agatgtccagattagataaaagtaaagtgattaacagcgcattagagctg cttaatgaggtcggaatcgaaggtttaacaacccgtaaactcgcccagaa gctaggtgtagagcagcctacattgtattggcatgtaaaaaataagcggg ctttgctcgacgccttagccattgagatgttagataggcaccatactcac ttttgccctttagaaggggaaagctggcaagatttttttacgtaataacgc taaaagttttagatgtgctttactaagtcatcgcgatggagcaaaagtac atttaggtacacggcctacagaaaaacagtatgaaactctcgaaaatcaa ttagcctttttatgccaacaaggtttttcactagagaatgcattatatgc actcagcgctgtggggcattttactttaggttgcgtattggaagatcaag agcatcaagtcgctaaagaagaaagggaaacacctactactgatagtatg ccgccattattacgacaagctatcgaattatttgatcaccaaggtgcaga gccagccttcttattcggccttgaattgatcatatgcggattagaaaaac aacttaaatgtgaaagtgggtccgctgcaaacgacgaaaactacgcttta gtagcttaataacactgatagtgctagtgtagatcactactagagccagg -continued catcaaataaaacgaaaggctcagtcgaaagactgggcctttcgttttat ctgttgtttgtcggtgaacgctctctactagagtcacactggctcacctt cgggtgggcctttctgcgtttatatactagagtccctatcagtgatagag attgacatccctatcagtgatagagatactgagcactactagagaaagag gagaaatactagatgcgtaaaggagaagaacttttcactggagttgtccc aattcttgttgaattagatggtgatgttaatgggcacaaattttctgtca gtggagagggtgaaggtgatgcaacatacggaaaacttacccttaaattt atttgcactactggaaaactacctgttccatggccaacacttgtcactac tttcggttatggtgttcaatgctttgcgagatacccagatcatatgaaac agcatgactttttcaagagtgccatgcccgaaggttatgtacaggaaaga actatatttttcaaagatgacgggaactacaagacacgtgctgaagtcaa gtttgaaggtgatacccttgttaatagaatcgagttaaaaggtattgatt ttaaagaagatggaaacattcttggacacaaattggaatacaactataac tcacacaatgtatacatcatggcagacaaacaaaagaatggaatcaaagt taacttcaaaattagacacaacattgaagatggaagcgttcaactagcag accattatcaacaaaatactccaattggcgatggccctgtccttttacca gacaaccattacctgtccacacaatctgccctttcgaaagatcccaacga aaagagagaccacatggtccttcttgagtttgtaacagctgctgggatta cacatggcatggatgaactatacaaataataatactagagaaagaggaga aatactagatgaaatctaacaatgcgctcatcgtcatcctcggcaccgtc accctggatgctgtaggcataggcttggttatgccggtactgccgggcct cttgcgggatatcgtccattccgacagcatcgccagtcactatggcgtgc tgctagcgctatatgcgttgatgcaatttctatgcgcacccgttctcgga gcactgtccgaccgctttggccgccgcccagtcctgctcgcttcgctact tggagccactatcgactacgcgatcatggcgaccacacccgtcctgtgga tcctctacgccggacgcatcgtggccggcatcaccggcgccacaggtgcg gttgctggcgcctatatcgccgacatcaccgatggggaagatcgggctcg ccacttcgggctcatgagcgcttgtttcggcgtgggtatggtggcaggcc ccgtggccgggggactgttgggcgccatctccttgcatgcaccattcctt gcggcggcggtgctcaacggcctcaacctactactgggctgcttcctaat gcaggagtcgcataagggagagcgtcgaccgatgcccttgagagccttca acccagtcagctccttccggtgggcgcggggcatgactatcgtcgccgca cttatgactgtcttctttatcatgcaactcgtaggacaggtgccggcagc gctctgggtcattttcggcgaggaccgctttcgctggagcgcgacgatga tcggcctgtcgcttgcggtattcggaatcttgcacgccctcgctcaagcc ttcgtcactggccccgccaccaaacgtttcggcgagaagcaggccattat cgccggcatggcggccgacgcgctgggctacgtcttgctggcgttcgcga cgcgaggctggatggccttccccattatgattcttctcgcttccggcggc atcgggatgcccgcgttgcaggccatgctgtccaggcaggtagatgacga ccatcagggacagcttcaaggatcgctcgcggctcttaccagcctaactt cgatcattggaccgctgatcgtcacggcgatttatgccgcctcggcgagc -continued acatggaacgggttggcatggattgtaggcgccgccctataccttgtctg cctccccgcgttgcgtcgcggtgcatggagccgggccacctcgacctaa J85209- Composite part to detect 3OC6HSL and produce RFP, or in the absence of 3OC6HSL to produce GFP and cm resistance. Uses TetR/Ptet regulatory mechanism. Same as J85204 but with Chloramphenicol resistance added. J58208 is a sister part with tetracycline resistance instead:

(SEQ ID NO: 9)

tggtgcaaaacctttcgcggtatggcatgatagcgcctactagagaaaga ggagaaatactagatgaaaaacataaatgccgacgacacatacagaataa ttaataaaattaaagcttgtagaagcaataatgatattaatcaatgctta tctgatatgactaaaatggtacattgtgaatattatttactcgcgatcat ttatcctcattctatggttaaatctgatatttcaatcctagataattacc ctaaaaaatggaggcaatattatgatgacgctaatttaataaaatatgat cctatagtagattattctaactccaatcattcaccaattaattggaatat atttgaaaacaatgctgtaaataaaaaatctccaaatgtaattaaagaag cgaaaacatcaggtcttatcactgggtttagtttccctattcatacggct aacaatggcttcggaatgcttagttttgcacattcagaaaaagacaacta tatagatagtttatttttacatgcgtgtatgaacataccattaattgttc cttctctagttgataattatcgaaaaataaatatagcaaataataaatca aacaacgatttaaccaaaagagaaaaagaatgtttagcgtgggcatgcga aggaaaaagctcttgggatatttcaaaaatattaggttgcagtgagcgta ctgtcactttccatttaaccaatgcgcaaatgaaactcaatacaacaaac cgctgccaaagtatttctaaagcaattttaacaggagcaattgattgccc atactttaaaaattaataacactgatagtgctagtgtagatcactactag agccaggcatcaaataaaacgaaaggctcagtcgaaagactgggcctttc gttttatctgttgtttgtcggtgaacgctctctactagagtcacactggc tcaccttcgggtgggcctttctgcgtttatatactagagacctgtaggat cgtacaggtttacgcaagaaaatggtttgttatagtcgaataaatactag agaaagaggagaaatactagatggcttcctccgaagacgttatcaaagag ttcatgcgtttcaaagttcgtatggaaggttccgttaacggtcacgagtt cgaaatcgaaggtgaaggtgaaggtcgtccgtacgaaggtacccagaccg ctaaactgaaagttaccaaaggtggtccgctgccgttcgcttgggacatc ctgtccccgcagttccagtacggttccaaagcttacgttaaacacccggc tgacatcccggactacctgaaactgtccttcccggaaggtttcaaatggg aacgtgttatgaacttcgaagacggtggtgttgttaccgttacccaggac tcctccctgcaagacggtgagttcatctacaaagttaaactgcgtggtac caacttcccgtccgacggtccggttatgcagaaaaaaaccatgggttggg aagcttccaccgaacgtatgtacccggaagacggtgctctgaaaggtgaa atcaaaatgcgtctgaaactgaaagacggtggtcactacgacgctgaagt taaaaccacctacatggctaaaaaaccggttcagctgccgggtgcttaca aaaccgacatcaaactggacatcacctcccacaacgaagactacaccatc gttgaacagtacgaacgtgctgaaggtcgtcactccaccggtgcttaata -continued acgctgatagtgctagtgtagatcgctactagagaaagaggagaaatact agatgtccagattagataaaagtaaagtgattaacagcgcattagagctg cttaatgaggtcggaatcgaaggtttaacaacccgtaaactcgcccagaa gctaggtgtagagcagcctacattgtattggcatgtaaaaaataagcggg ctttgctcgacgccttagccattgagatgttagataggcaccatactcac ttttgccctttagaaggggaaagctggcaagatttttacgtaataacgc taaaagttttagatgtgctttactaagtcatcgcgatggagcaaaagtac atttaggtacacggcctacagaaaaacagtatgaaactctcgaaaatcaa ttagcctttttatgccaacaaggtttttcactagagaatgcattatatgc actcagcgctgtggggcattttactttaggttgcgtattggaagatcaag agcatcaagtcgctaaagaagaaagggaaacacctactactgatagtatg ccgccattattacgacaagctatcgaattatttgatcaccaaggtgcaga gccagccttcttattcggccttgaattgatcatatgcggattagaaaaac aacttaaatgtgaaagtgggtccgctgcaaacgacgaaaactacgcttta gtagcttaataacactgatagtgctagtgtagatcactactagagccagg catcaaataaaacgaaaggctcagtcgaaagactgggcctttcgttttat ctgttgtttgtcggtgaacgctctctactagagtcacactggctcacctt cgggtgggcctttctgcgtttatatactagagtccctatcagtgatagag attgacatccctatcagtgatagagatactgagcactactagagaaagag gagaaatactagatgcgtaaaggagaagaacttttcactggagttgtccc aattcttgttgaattagatggtgatgttaatgggcacaaattttctgtca gtggagagggtgaaggtgatgcaacatacggaaaacttacccttaaattt atttgcactactggaaaactacctgttccatggccaacacttgtcactac tttcggttatggtgttcaatgctttgcgagatacccagatcatatgaaac agcatgactttttcaagagtgccatgcccgaaggttatgtacaggaaaga actatatttttcaaagatgacgggaactacaagacacgtgctgaagtcaa gtttgaaggtgatacccttgttaatagaatcgagttaaaaggtattgatt ttaaagaagatggaaacattcttggacacaaattggaatacaactataac tcacacaatgtatacatcatggcagacaaacaaaagaatggaatcaaagt taacttcaaaattagacacaacattgaagatggaagcgttcaactagcag accattatcaacaaaatactccaattggcgatggccctgtccttttacca gacaaccattacctgtccacacaatctgccctttcgaaagatcccaacga aaagagagaccacatggtccttcttgagtttgtaacagctgctgggatta cacatggcatggatgaactatacaaataataatactagagaaagaggaga aatactagatggagaaaaaaatcactggatataccaccgttgatatatcc caatggcatcgtaaagaacattttgaggcatttcagtcagttgctcaatg tacctataaccagaccgttcagctggatattacggcctttttaaagaccg taaagaaaaataagcacaagttttatccggcctttattcacattcttgcc cgcctgatgaatgctcatccggaatttcgtatggcaatgaaagacggtga -continued gctggtgatatgggatagtgttcacccttgttacaccgttttccatgagc aaactgaaacgttttcatcgctctggagtgaataccacgacgatttccgg cagtttctacacatatattcgcaagatgtggcgtgttacggtgaaaacct ggcctatttccctaaagggtttattgagaatatgtttttcgtctcagcca atccctgggtgagtttcaccagttttgatttaaacgtggccaatatggac aacttcttcgcccccgttttcaccatgggcaaatattatacgcaaggcga caaggtgctgatgccgctggcgattcaggttcatcatgccgtttgtgatg gcttccatgtcggcagaatgcttaatgaattacaacagtactgcgatgag tggcagggcggggcgtaa J85220- GFP marker and chloramphenicol resistance to be used in a chromosomal integration test:

(SEQ ID NO: 10)

tccctatcagtgatagagattgacatccctatcagtgatagagatactga gcactactagagaaagaggagaaatactagatgcgtaaaggagaagaact tttcactggagttgtcccaattcttgttgaattagatggtgatgttaatg ggcacaaattttctgtcagtggagagggtgaaggtgatgcaacatacgga aaacttacccttaaatttatttgcactactggaaaactacctgttccatg gccaacacttgtcactactttcggttatggtgttcaatgctttgcgagat acccagatcatatgaaacagcatgactttttcaagagtgccatgcccgaa ggttatgtacaggaaagaactatatttttcaaagatgacgggaactacaa gacacgtgctgaagtcaagtttgaaggtgatacccttgttaatagaatcg agttaaaaggtattgattttaaagaagatggaaacattcttggacacaaa ttggaatacaactataactcacacaatgtatacatcatggcagacaaaca aaagaatggaatcaaagttaacttcaaaattagacacaacattgaagatg gaagcgttcaactagcagaccattatcaacaaaatactccaattggcgat ggccctgtccttttaccagacaaccattacctgtccacacaatctgccct ttcgaaagatcccaacgaaaagagagaccacatggtccttcttgagtttg taacagctgctgggattacacatggcatggatgaactatacaaataataa tactagagaaagaggagaaatactagatggagaaaaaaatcactggatat accaccgttgatatatcccaatggcatcgtaaagaacattttgaggcatt tcagtcagttgctcaatgtacctataaccagaccgttcagctggatatta cggcctttttaaagaccgtaaagaaaaataagcacaagttttatccggcc tttattcacattcttgcccgcctgatgaatgctcatccggaatttcgtat ggcaatgaaagacggtgagctggtgatatgggatagtgttcacccttgtt acaccgttttccatgagcaaactgaaacgttttcatcgctctggagtgaa taccacgacgatttccggcagtttctacacatatattcgcaagatgtggc gtgttacggtgaaaacctggcctatttccctaaagggtttattgagaata tgtttttcgtctcagccaatccctgggtgagtttcaccagttttgattta aacgtggccaatatggacaacttcttcgcccccgttttcaccatgggcaa atattatacgcaaggcgacaaggtgctgatgccgctggcgattcaggttc atcatgccgtttgtgatggcttccatgtcggcagaatgcttaatgaatta caacagtactgcgatgagtggcagggcggggcgtaa J85221- GFP marker and kanamycin resistance cassette to be used in a chromosomal integration test:

(SEQ ID NO: 11)

tccctatcagtgatagagattgacatccctatcagtgatagagatactga gcactactagagaaagaggagaaatactagatgcgtaaaggagaagaact tttcactggagttgtcccaattcttgttgaattagatggtgatgttaatg ggcacaaattttctgtcagtggagagggtgaaggtgatgcaacatacgga aaacttacccttaaatttatttgcactactggaaaactacctgttccatg gccaacacttgtcactactttcggttatggtgttcaatgctttgcgagat acccagatcatatgaaacagcatgactttttcaagagtgccatgcccgaa ggttatgtacaggaaagaactatatttttcaaagatgacgggaactacaa gacacgtgctgaagtcaagtttgaaggtgatacccttgttaatagaatcg agttaaaaggtattgattttaaagaagatggaaacattcttggacacaaa ttggaatacaactataactcacacaatgtatacatcatggcagacaaaca aaagaatggaatcaaagttaacttcaaaattagacacaacattgaagatg gaagcgttcaactagcagaccattatcaacaaaatactccaattggcgat ggccctgtccttttaccagacaaccattacctgtccacacaatctgccct ttcgaaagatcccaacgaaaagagagaccacatggtccttcttgagtttg taacagctgctgggattacacatggcatggatgaactatacaaataataa tactagagctgatccttcaactcagcaaaagttcgatttattcaacaaag ccacgttgtgtctcaaaatctctgatgttacattgcacaagataaaaata tatcatcatgaacaataaaactgtctgcttacataaacagtaatacaagg ggtgttatgagccatattcaacgggaaacgtcttgctcccgtccgcgctt aaactccaacatggacgctgatttatatgggtataaatgggctcgcgata atgtcgggcaatcaggtgcgacaatctatcgcttgtatgggaagcccgat gcgccagagttgtttctgaaacatggcaaaggtagcgttgccaatgatgt tacagatgagatggtccgtctcaactggctgacggagtttatgcctctcc cgaccatcaagcattttatccgtactcctgatgatgcgtggttactcacc accgcgattcctgggaaaacagccttccaggtattagaagaatatcctga ttcaggtgaaaatattgttgatgcgctggccgtgttcctgcgccggttac attcgattcctgtttgtaattgtccttttaacagcgatcgtgtatttcgt cttgctcaggcgcaatcacgcatgaataacggtttggttgatgcgagtga ttttgatgacgagcgtaatggctggcctgttgaacaagtctggaaagaaa tgcacaagctcttgccattctcaccggattcagtcgtcactcatggtgat ttctcacttgataaccttatttttgacgaggggaaattaataggttgtat tgatgttggacgggtcggaatcgcagaccgttaccaggaccttgccattc tttggaactgcctcggtgagttttctccttcattacagaaacggcttttt caaaaatatggtattgataatcctgatatgaataaattgcagtttcattt gatgctcgatgagtttttctaataa Additional Sequences:

BioBrick_attB_integration_FWD
(SEQ ID NO: 12)
AGC CAA CTT AAATTA ATG AAA AAATGT TAT TAATCG

TTG AGA ATT CGC GGC CGCTTC TAG

BioBrick_attB_integration_REV
(SEQ ID NO: 13)
TAA CTT ATT GCG ATATGGTTA CAT TAA GGG CAA AGC

ATC TCT GCA GCG GCC GCT ACT AGT lacZ::BioBrick forward
(SEQ ID NO: 14)
TGACCATGATTACGGATTCACTGGCCGTCGTTTTACAACGTCGTG gaattcgcggccgcttctag lacZ::BioBRick reverse
(SEQ ID NO: 15)
GTGCTGCAAGGCGATTAAGTTGGGTAACGCCAGGGTTTTCCCAGT ctgcagcggccgctactagt Examples of oligonucleotides for MAGE:

cat_restore76thio4 (* phosphorothioate)
(SEQ ID NO: 16)
T*G*G ATA TAC CAC CGT TGA TAT ATC CCA ATG GCA

TCG TAA AGA ACA TTT TGA GGC ATT TCA GTC AGT

TGC TCA ATG TAC CTA TAA CCA G*A*C bla_restore76thio4
(SEQ ID NO: 17)
A*G*T GCT CAT CAT TGG AAA ACG TTC TTC GGG GCG

AAA ACT CTC AAG GAT CTT ACC GCT GTT GAG ATC

CAG TTC GAT GTA ACC CAC TCG T*G*C

-continued

LacZstop-76*4S: (The "ATG" shows the start codon for the lacZ gene; the TGA is the stop codon (the underlined base is the one being flipped from G to A). The * shows a phosphorothioate bond:
(SEQ ID NO: 18)
T*A*ACAATTTCACACAGGAAACAGCTatgACCATGATTACGGATTCACT

GGCCGTCGTTTTACAACGTCGTGACTGAGAAAACCCTGGC*G*T bla_restore76thio4:
(SEQ ID NO: 19)
A*G*TGCTCATCATTGGAAAACGTTCTTCGGGGCGAAAACTCTCAAGGAT

CTTACCGCTGTTGAGATCCAGTTCGATGTAACCCACTCGT*G*C cat_restore76thio4:
(SEQ ID NO: 20)
T*G*GATATACCACCGTTGATATATCCCAATGGCATCGTAAAGAACATTT

TGAGGCATTTCAGTCAGTTGCTCAATGTACCTATAACCAG*A*C

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention.

Accordingly, the foregoing description and drawings are by way of example only. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the specific purpose mentioned herein.

What is claimed is:

1. A Bio-Field Programmable Gate Array (BioFPGA) comprising a biological circuit comprising recombinant DNA that includes a plurality of reconfigurable target regions, wherein each reconfigurable target region comprises a prefix recombination site and a suffix recombination site surrounding at least one selection marker and/or counterselection marker, wherein the prefix recombination site and the suffix recombination site each comprise an overlap sequence and a unique address sequence, wherein the overlap sequence in the suffix recombination site of each reconfigurable target region in the plurality of reconfigurable target regions is the same, and wherein the at least one selection and/or counterselection marker in at least one of the reconfigurable target regions is disabled.

2. The BioFPGA of claim 1, wherein the prefix recombination site and the suffix recombination site each comprise an att (attachment) site.

3. The BioFPGA of claim 1, wherein the recombinant DNA is chromosomal DNA or plasmid DNA.

4. A kit comprising the BioFPGA of claim 1.

5. The kit of claim 4, wherein the prefix recombination site and the suffix recombination site each comprise a multiplex automated genome engineering (MAGE) target site modifiable by one or more MAGE oligonucleotides.

6. The kit of claim 4, wherein the kit further comprises one or more genetic elements capable of recombining with the BioFPGA.

7. A method comprising:

providing a BioFPGA of claim 1;

conducting multiplex automated genome engineering (MAGE) on one or more of the prefix recombination site and the suffix recombination site in the BioFPGA, thereby generating a reconfigured BioFPGA;

providing a plasmid that comprises one or more of the prefix recombination site and the suffix recombination site matching one or more of the prefix recombination site and the suffix recombination site on the reconfigured BioFPGA; and conducting recombination between the plasmid and the reconfigured BioFPGA.

8. A Bio-Field Programmable Gate Array (BioFPGA) comprising:

recombinant DNA that includes a plurality of reconfigurable target regions, wherein each reconfigurable target region comprises a prefix recombination site and a suffix recombination site that is each modifiable by multiplex automated genome engineering (MAGE) using a plurality of MAGE oligonucleotides to produce a plurality of reconfigured target regions;

wherein a first reconfigurable target region is modifiable with a first plurality of MAGE oligonucleotides to produce a first reconfigured target region;

wherein a second reconfigurable target region is modifiable with a second plurality of MAGE oligonucleotides to produce a second reconfigured target region;

wherein the first reconfigurable target region is not modifiable with the second plurality of MAGE oligonucleotides;

wherein the prefix recombination site and the suffix recombination site each comprise an overlap sequence; and wherein the overlap sequence in the suffix recombination site of each reconfigurable target region in the plurality of reconfigurable target regions is the same.

9. The BioFPGA according to claim 8, wherein the first reconfigurable target region is modifiable with a fourth plurality of MAGE oligonucleotides to produce a fourth reconfigured target region that comprises a prefix recombination site and a suffix recombination site that have the same specificity as the prefix recombination site and the suffix recombination site in the second reconfigured target region.

10. The BioFPGA according to claim 8, wherein the reconfigured target regions comprise att (attachment) sites.

11. The BioFPGA of claim 1, wherein the prefix recombination site and the suffix recombination site each comprise a multiplex automated genome engineering (MAGE) target site modifiable by one or more MAGE oligonucleotides to produce an engineered prefix recombination site and an engineered suffix recombination site, wherein the engineered prefix recombination site and the engineered suffix recombination site only recombine with a genetic element that contains a matching recombination site.

12. The BioFPGA of claim 1, wherein the unique address sequence comprises 30-100 nucleotides.

13. The BioFPGA of claim 12, wherein the unique address sequence comprises at least 65 nucleotides.

14. The BioFPGA of claim 11, wherein the MAGE target site contains the unique address sequence.

15. The BioFPGA of claim 8, wherein the prefix recombination site and the suffix recombination site of the first reconfigurable target region are each modifiable with a third plurality of MAGE oligonucleotides to produce a third reconfigured target region that is different from the first reconfigured target region.

16. The BioFPGA of claim 8, wherein each reconfigurable target region further comprises at least one selection marker and/or counterselection marker, and wherein the selection marker and/or counterselection marker is surrounded by the prefix recombination site and the suffix recombination site, and wherein the selection or counterselection marker in at least one of the reconfigurable target regions is disabled.

17. The BioFPGA of claim 9, wherein each reconfigurable target region further comprises at least one selection marker and/or counterselection marker, and wherein the selection marker and/or counterselection marker is surrounded by the prefix recombination site and the suffix recombination site.

18. The BioFPGA of claim 15, wherein each reconfigurable target region further comprises at least one selection marker and/or counterselection marker, and wherein the selection marker and/or counterselection marker is surrounded by the prefix recombination site and the suffix recombination site.

19. The BioFPGA of claim 8, wherein the prefix recombination site and the suffix recombination site each comprises an att (attachment) site.

20. The BioFPGA of claim 11, wherein each MAGE target site comprises at least a portion of the suffix recombination site, and wherein one or more MAGE oligonucleotides introduces at least one mutation in the overlap sequence in the suffix recombination site.

21. A kit comprising the BioFPGA of claim 20, further comprising one or more MAGE oligonucleotides that introduce one or more mutations that change the overlap sequence, change the specificity, and/or change the recombination efficiency of the prefix recombination site or the suffix recombination site.

22. The kit of claim 20, wherein the selection or counterselection marker that is disabled comprises a MAGE target site that is modifiable by one or more MAGE oligonucleotides, wherein the one or more MAGE oligonucleotides introduce one or more mutations in the selection or counterselection marker that is disabled, optionally, wherein the one or more mutations remove a stop codon from the selection or counterselection marker that is disabled.

23. The kit of claim 20, wherein the selection and/or counterselection marker that is not disabled comprises a MAGE target site that is modifiable by one or more MAGE oligonucleotides, wherein the one or more MAGE oligonucleotides introduce one or more mutations in the selection and/or counterselection marker that is not disabled, optionally, wherein the one or more mutations add a stop codon to the selection and/or counterselection marker that is not disabled.

* * * * *

SEQUENCE LISTING

<160> NUMBER OF SEQ ID NOS: 55

<210> SEQ ID NO 1
<211> LENGTH: 738
<212> TYPE: DNA
<213> ORGANISM: Artificial Sequence
<220> FEATURE:
<223> OTHER INFORMATION: Synthetic Polynucleotide

<400> SEQUENCE: 1
aaagaggaga aatactagat gcgtaaagga gaagaacttt tcactggagt tgtcccaatt 60
cttgttgaat tagatggtga tgttaatggg cacaaatttt ctgtcagtgg agagggtgaa 120
ggtgatgcaa catacggaaa acttaccctt aaatttattt gcactactgg aaaactacct 180
gttccatggc caacacttgt cactactttc ggttatggtg ttcaatgctt tgcgagatac 240
ccagatcata tgaaacagca tgactttttc aagagtgcca tgcccgaagg ttatgtacag 300
gaaagaacta tatttttcaa agatgacggg aactacaaga cacgtgctga agtcaagttt 360
gaaggtgata cccttgttaa tagaatcgag ttaaaaggta ttgattttaa agaagatgga 420
aacattcttg gacacaaatt ggaatacaac tataactcac acaatgtata catcatggca 480
gacaaacaaa agaatggaat caaagttaac ttcaaaatta gacacaacat tgaagatgga 540
agcgttcaac tagcagacca ttatcaacaa aatactccaa ttggcgatgg ccctgtcctt 600

-continued

```
ttaccagaca accattacct gtccacacaa tctgcccttt cgaaagatcc caacgaaaag    660

agagaccaca tggtccttct tgagtttgta acagctgctg ggattacaca tggcatggat    720

gaactataca aataataa                                                  738
```

<210> SEQ ID NO 2
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 2

```
tccctatcag tgatagagat tgacatccct atcagtgata gagatactga gcactactag     60

agaaagagga gaaatactag atgcgtaaag gagaagaact tttcactgga gttgtcccaa    120

ttcttgttga attagatggt gatgttaatg ggcacaaatt ttctgtcagt ggagagggtg    180

aaggtgatgc aacatacgga aaacttaccc ttaaatttat ttgcactact ggaaaactac    240

ctgttccatg gccaacactt gtcactactt tcggttatgg tgttcaatgc tttgcgagat    300

acccagatca tatgaaacag catgactttt tcaagagtgc catgcccgaa ggttatgtac    360

aggaaagaac tatatttttc aaagatgacg ggaactacaa gacacgtgct gaagtcaagt    420

ttgaaggtga tacccttgtt aatagaatcg agttaaaagg tattgatttt aaagaagatg    480

gaaacattct tggacacaaa ttggaataca actataactc acacaatgta tacatcatgg    540

cagacaaaca aaagaatgga atcaaagtta acttcaaaat tagacacaac attgaagatg    600

gaagcgttca actagcagac cattatcaac aaaatactcc aattggcgat ggccctgtcc    660

ttttaccaga caaccattac ctgtccacac aatctgccct ttcgaaagat cccaacgaaa    720

agagagacca catggtcctt cttgagtttg taacagctgc tgggattaca catggcatgg    780

atgaactata caaataataa                                                800
```

<210> SEQ ID NO 3
<211> LENGTH: 2624
<212> TYPE: DNA
<213> ORGANISM: Artificial Sequence
<220> FEATURE:
<223> OTHER INFORMATION: Synthetic Polynucleotide

<400> SEQUENCE: 3

```
tggtgcaaaa cctttcgcgg tatggcatga tagcgcctac tagagaaaga ggagaaatac     60

tagatgaaaa acataaatgc cgacgacaca tacagaataa ttaataaaat taaagcttgt    120

agaagcaata atgatattaa tcaatgctta tctgatatga ctaaaatggt acattgtgaa    180

tattatttac tcgcgatcat ttatcctcat tctatggtta aatctgatat ttcaatccta    240

gataattacc ctaaaaaatg gaggcaatat tatgatgacg ctaatttaat aaaatatgat    300

cctatagtag attattctaa ctccaatcat tcaccaatta attggaatat atttgaaaac    360

aatgctgtaa ataaaaaatc tccaaatgta attaaagaag cgaaaacatc aggtcttatc    420

actgggttta gtttccctat tcatacggct aacaatggct tcggaatgct tagttttgca    480

cattcagaaa aagacaacta tatagatagt ttattttac atgcgtgtat gaacatacca    540

ttaattgttc cttctctagt tgataattat cgaaaaataa atatagcaaa taataaatca    600

aacaacgatt taaccaaaag agaaaaagaa tgtttagcgt gggcatgcga aggaaaaagc    660

tcttgggata tttcaaaaat attaggttgc agtgagcgta ctgtcacttt ccatttaacc    720

aatgcgcaaa tgaaactcaa tacaacaaac cgctgccaaa gtatttctaa agcaatttta    780
```

-continued

```
acaggagcaa ttgattgccc atactttaaa aattaataac actgatagtg ctagtgtaga    840

tcactactag agccaggcat caaataaaac gaaaggctca gtcgaaagac tgggcctttc    900

gttttatctg ttgtttgtcg gtgaacgctc tctactagag tcacactggc tcaccttcgg    960

gtgggccttt ctgcgtttat atactagaga cctgtaggat cgtacaggtt tacgcaagaa   1020

aatggtttgt tatagtcgaa taaatactag agaaagagga gaaatactag atggcttcct   1080

ccgaagacgt tatcaaagag ttcatgcgtt tcaaagttcg tatggaaggt tccgttaacg   1140

gtcacgagtt cgaaatcgaa ggtgaaggtg aaggtcgtcc gtacgaaggt acccagaccg   1200

ctaaactgaa agttaccaaa ggtggtccgc tgccgttcgc ttgggacatc ctgtccccgc   1260

agttccagta cggttccaaa gcttacgtta aacacccggc tgacatcccg gactacctga   1320

aactgtcctt cccggaaggt ttcaaatggg aacgtgttat gaacttcgaa gacggtggtg   1380

ttgttaccgt tacccaggac tcctccctgc aagacggtga gttcatctac aaagttaaac   1440

tgcgtggtac caacttcccg tccgacggtc cggttatgca gaaaaaaacc atgggttggg   1500

aagcttccac cgaacgtatg tacccggaag acggtgctct gaaaggtgaa atcaaaatgc   1560

gtctgaaact gaaagacggt ggtcactacg acgctgaagt taaaaccacc tacatggcta   1620

aaaaaccggt tcagctgccg ggtgcttaca aaaccgacat caaactggac atcacctccc   1680

acaacgaaga ctacaccatc gttgaacagt acgaacgtgc tgaaggtcgt cactccaccg   1740

gtgcttaata acgctgatag tgctagtgta gatcgctact agagaaagag gagaaatact   1800

agatgtccag attagataaa agtaaagtga ttaacagcgc attagagctg cttaatgagg   1860

tcggaatcga aggtttaaca acccgtaaac tcgcccagaa gctaggtgta gagcagccta   1920

cattgtattg gcatgtaaaa aataagcggg ctttgctcga cgccttagcc attgagatgt   1980

tagataggca ccatactcac ttttgccctt tagaagggga aagctggcaa gatttttac    2040

gtaataacgc taaaagtttt agatgtgctt tactaagtca tcgcgatgga gcaaaagtac   2100

atttaggtac acggcctaca gaaaaacagt atgaaactct cgaaaatcaa ttagcctttt   2160

tatgccaaca aggtttttca ctagagaatg cattatatgc actcagcgct gtggggcatt   2220

ttactttagg ttgcgtattg gaagatcaag agcatcaagt cgctaaagaa gaaagggaaa   2280

cacctactac tgatagtatg ccgccattat tacgacaagc tatcgaatta tttgatcacc   2340

aaggtgcaga gccagccttc ttattcggcc ttgaattgat catatgcgga ttagaaaaac   2400

aacttaaatg tgaaagtggg tccgctgcaa acgacgaaaa ctacgcttta gtagcttaat   2460

aacactgata gtgctagtgt agatcactac tagagccagg catcaaataa aacgaaaggc   2520

tcagtcgaaa gactgggcct ttcgttttat ctgttgtttg tcggtgaacg ctctctacta   2580

gagtcacact ggctcacctt cgggtgggcc tttctgcgtt tata                    2624
```

<210> SEQ ID NO 4
<211> LENGTH: 3432
<212> TYPE: DNA
<213> ORGANISM: Artificial Sequence
<220> FEATURE:
<223> OTHER INFORMATION: Synthetic Polynucleotide

<400> SEQUENCE: 4

```
tggtgcaaaa cctttcgcgg tatggcatga tagcgcctac tagagaaaga ggagaaatac     60

tagatgaaaa acataaatgc cgacgacaca tacagaataa ttaataaaat taaagcttgt    120

agaagcaata atgatattaa tcaatgctta tctgatatga ctaaaatggt acattgtgaa    180

tattatttac tcgcgatcat ttatcctcat tctatggtta aatctgatat ttcaatccta    240
```

-continued

```
gataattacc ctaaaaaatg gaggcaatat tatgatgacg ctaatttaat aaaatatgat    300
cctatagtag attattctaa ctccaatcat tcaccaatta attggaatat atttgaaaac    360
aatgctgtaa ataaaaaatc tccaaatgta attaaagaag cgaaaacatc aggtcttatc    420
actgggttta gtttccctat tcatacggct aacaatggct tcggaatgct tagttttgca    480
cattcagaaa aagacaacta tatagatagt ttatttttac atgcgtgtat gaacatacca    540
ttaattgttc cttctctagt tgataattat cgaaaaataa atatagcaaa taataaatca    600
aacaacgatt taaccaaaag agaaaaagaa tgtttagcgt gggcatgcga aggaaaaagc    660
tcttgggata tttcaaaaat attaggttgc agtgagcgta ctgtcacttt ccatttaacc    720
aatgcgcaaa tgaaactcaa tacaacaaac cgctgccaaa gtatttctaa agcaatttta    780
acaggagcaa ttgattgccc atactttaaa aattaataac actgatagtg ctagtgtaga    840
tcactactag agccaggcat caaataaaac gaaaggctca gtcgaaagac tgggcctttc    900
gttttatctg ttgtttgtcg gtgaacgctc tctactagag tcacactggc tcaccttcgg    960
gtgggccttt ctgcgtttat atactagaga cctgtaggat cgtacaggtt tacgcaagaa   1020
aatggtttgt tatagtcgaa taaatactag agaaagagga gaaatactag atggcttcct   1080
ccgaagacgt tatcaaagag ttcatgcgtt tcaaagttcg tatggaaggt tccgttaacg   1140
gtcacgagtt cgaaatcgaa ggtgaaggtg aaggtcgtcc gtacgaaggt acccagaccg   1200
ctaaactgaa agttaccaaa ggtggtccgc tgccgttcgc ttgggacatc ctgtccccgc   1260
agttccagta cggttccaaa gcttacgtta aacacccggc tgacatcccg gactacctga   1320
aactgtcctt cccggaaggt ttcaaatggg aacgtgttat gaacttcgaa gacggtggtg   1380
ttgttaccgt tacccaggac tcctccctgc aagacggtga gttcatctac aaagttaaac   1440
tgcgtggtac caacttcccg tccgacggtc cggttatgca gaaaaaaacc atgggttggg   1500
aagcttccac cgaacgtatg tacccggaag acggtgctct gaaaggtgaa atcaaaatgc   1560
gtctgaaact gaaagacggt ggtcactacg acgctgaagt taaaaccacc tacatggcta   1620
aaaaaccggt tcagctgccg ggtgcttaca aaaccgacat caaactggac atcacctccc   1680
acaacgaaga ctacaccatc gttgaacagt acgaacgtgc tgaaggtcgt cactccaccg   1740
gtgcttaata acgctgatag tgctagtgta gatcgctact agagaaagag gagaaatact   1800
agatgtccag attagataaa agtaaagtga ttaacagcgc attagagctg cttaatgagg   1860
tcggaatcga aggtttaaca acccgtaaac tcgcccagaa gctaggtgta gagcagccta   1920
cattgtattg gcatgtaaaa aataagcggg ctttgctcga cgccttagcc attgagatgt   1980
tagataggca ccatactcac ttttgccctt tagaagggga aagctggcaa gatttttac   2040
gtaataacgc taaaagtttt agatgtgctt tactaagtca tcgcgatgga gcaaaagtac   2100
atttaggtac acggcctaca gaaaaacagt atgaaactct cgaaaatcaa ttagcctttt   2160
tatgccaaca aggtttttca ctagagaatg cattatatgc actcagcgct gtggggcatt   2220
ttactttagg ttgcgtattg gaagatcaag agcatcaagt cgctaaagaa gaaagggaaa   2280
cacctactac tgatagtatg ccgccattat tacgacaagc tatcgaatta tttgatcacc   2340
aaggtgcaga gccagccttc ttattcggcc ttgaattgat catatgcgga ttagaaaaac   2400
aacttaaatg tgaaagtggg tccgctgcaa acgacgaaaa ctacgcttta gtagcttaat   2460
aacactgata gtgctagtgt agatcactac tagagccagg catcaaataa aacgaaaggc   2520
tcagtcgaaa gactgggcct ttcgttttat ctgttgtttg tcggtgaacg ctctctacta   2580
gagtcacact ggctcacctt cgggtgggcc tttctgcgtt tatatactag agtccctatc   2640
```

-continued

```
agtgatagag attgacatcc ctatcagtga tagagatact gagcactact agagaaagag   2700

gagaaatact agatgcgtaa aggagaagaa cttttcactg gagttgtccc aattcttgtt   2760

gaattagatg gtgatgttaa tgggcacaaa ttttctgtca gtggagaggg tgaaggtgat   2820

gcaacatacg gaaaacttac ccttaaattt atttgcacta ctggaaaact acctgttcca   2880

tggccaacac ttgtcactac tttcggttat ggtgttcaat gctttgcgag atacccagat   2940

catatgaaac agcatgactt tttcaagagt gccatgcccg aaggttatgt acaggaaaga   3000

actatatttt tcaaagatga cgggaactac aagacacgtg ctgaagtcaa gtttgaaggt   3060

gataccottg ttaatagaat cgagttaaaa ggtattgatt ttaaagaaga tggaaacatt   3120

cttggacaca aattggaata caactataac tcacacaatg tatacatcat ggcagacaaa   3180

caaaagaatg gaatcaaagt taacttcaaa attagacaca acattgaaga tggaagcgtt   3240

caactagcag accattatca acaaaatact ccaattggcg atggccctgt ccttttacca   3300

gacaaccatt acctgtccac acaatctgcc ctttcgaaag atcccaacga aaagagagac   3360

cacatggtcc ttcttgagtt tgtaacagct gctgggatta cacatggcat ggatgaacta   3420

tacaaataat aa                                                       3432
```

<210> SEQ ID NO 5
<211> LENGTH: 3569
<212> TYPE: DNA
<213> ORGANISM: Artificial Sequence
<220> FEATURE:
<223> OTHER INFORMATION: Synthetic Polynucleotide

<400> SEQUENCE: 5

```
tggtgcaaaa cctttcgcgg tatggcatga tagcgcctac tagagaaaga ggagaaatac     60

tagatgaaaa acataaatgc cgacgacaca tacagaataa ttaataaaat taaagcttgt    120

agaagcaata atgatattaa tcaatgctta tctgatatga ctaaaatggt acattgtgaa    180

tattatttac tcgcgatcat ttatcctcat tctatggtta aatctgatat ttcaatccta    240

gataattacc ctaaaaaatg gaggcaatat tatgatgacg ctaatttaat aaaatatgat    300

cctatagtag attattctaa ctccaatcat tcaccaatta attggaatat atttgaaaac    360

aatgctgtaa ataaaaaatc tccaaatgta attaaagaag cgaaaacatc aggtcttatc    420

actgggttta gtttccctat tcatacggct aacaatggct tcggaatgct tagttttgca    480

cattcagaaa aagacaacta tatagatagt ttatttttac atgcgtgtat gaacatacca    540

ttaattgttc cttctctagt tgataattat cgaaaaataa atatagcaaa taataaatca    600

aacaacgatt taaccaaaag agaaaaagaa tgtttagcgt gggcatgcga aggaaaaagc    660

tcttgggata tttcaaaaat attaggttgc agtgagcgta ctgtcacttt ccatttaacc    720

aatgcgcaaa tgaaactcaa tacaacaaac cgctgccaaa gtatttctaa agcaatttta    780

acaggagcaa ttgattgccc atactttaaa aattaataac actgatagtg ctagtgtaga    840

tcactactag agccaggcat caaataaaac gaaaggctca gtcgaaagac tgggcctttc    900

gttttatctg ttgtttgtcg gtgaacgctc tctactagag tcacactggc tcaccttcgg    960

gtgggccttt ctgcgtttat atactagaga cctgtaggat cgtacaggtt tacgcaagaa   1020

aatggtttgt tatagtcgaa taaatactag agaaagagga gaaatactag atggcttcct   1080

ccgaagacgt tatcaaagag ttcatgcgtt tcaaagttcg tatggaaggt tccgttaacg   1140

gtcacgagtt cgaaatcgaa ggtgaaggtg aaggtcgtcc gtacgaaggt acccagaccg   1200

ctaaactgaa agttaccaaa ggtggtccgc tgccgttcgc ttgggacatc ctgtccccgc   1260
```

-continued

```
agttccagta cggttccaaa gcttacgtta aacacccggc tgacatcccg gactacctga   1320
aactgtcctt cccggaaggt ttcaaatggg aacgtgttat gaacttcgaa gacggtggtg   1380
ttgttaccgt tacccaggac tcctccctgc aagacggtga gttcatctac aaagttaaac   1440
tgcgtggtac caacttcccg tccgacggtc cggttatgca gaaaaaaacc atgggttggg   1500
aagcttccac cgaacgtatg tacccggaag acggtgctct gaaaggtgaa atcaaaatgc   1560
gtctgaaact gaaagacggt ggtcactacg acgctgaagt taaaaccacc tacatggcta   1620
aaaaaccggt tcagctgccg ggtgcttaca aaaccgacat caaactggac atcacctccc   1680
acaacgaaga ctacaccatc gttgaacagt acgaacgtgc tgaaggtcgt cactccaccg   1740
gtgcttaata acgctgatag tgctagtgta gatcgctact agagaaagag gagaaatact   1800
agatgtccag attagataaa agtaaagtga ttaacagcgc attagagctg cttaatgagg   1860
tcggaatcga aggtttaaca acccgtaaac tcgcccagaa gctaggtgta gagcagccta   1920
cattgtattg gcatgtaaaa aataagcggg ctttgctcga cgccttagcc attgagatgt   1980
tagataggca ccatactcac ttttgccctt tagaagggga aagctggcaa gatttttac    2040
gtaataacgc taaaagtttt agatgtgctt tactaagtca tcgcgatgga gcaaaagtac   2100
atttaggtac acggcctaca gaaaaacagt atgaaactct cgaaaatcaa ttagcctttt   2160
tatgccaaca aggtttttca ctagagaatg cattatatgc actcagcgct gtggggcatt   2220
ttactttagg ttgcgtattg gaagatcaag agcatcaagt cgctaaagaa gaaagggaaa   2280
cacctactac tgatagtatg ccgccattat tacgacaagc tatcgaatta tttgatcacc   2340
aaggtgcaga gccagccttc ttattcggcc ttgaattgat catatgcgga ttagaaaaac   2400
aacttaaatg tgaaagtggg tccgctgcaa acgacgaaaa ctacgcttta gtagcttaat   2460
aacactgata gtgctagtgt agatcactac tagagccagg catcaaataa aacgaaaggc   2520
tcagtcgaaa gactgggcct ttcgttttat ctgttgtttg tcggtgaacg ctctctacta   2580
gagtcacact ggctcacctt cgggtgggcc tttctgcgtt tatatactag agtccctatc   2640
agtgatagag attgacatcc ctatcagtga tagagatact gagcactact agagaaagag   2700
gagaaatact agatgcgtaa aggagaagaa cttttcactg gagttgtccc aattcttgtt   2760
gaattagatg gtgatgttaa tgggcacaaa ttttctgtca gtggagaggg tgaaggtgat   2820
gcaacatacg gaaaacttac ccttaaattt atttgcacta ctggaaaact acctgttcca   2880
tggccaacac ttgtcactac tttcggttat ggtgttcaat gctttgcgag atacccagat   2940
catatgaaac agcatgactt tttcaagagt gccatgcccg aaggttatgt acaggaaaga   3000
actatatttt tcaaagatga cgggaactac aagacacgtg ctgaagtcaa gtttgaaggt   3060
gataccettg ttaatagaat cgagttaaaa ggtattgatt ttaaagaaga tggaaacatt   3120
cttggacaca aattggaata caactataac tcacacaatg tatacatcat ggcagacaaa   3180
caaaagaatg gaatcaaagt taacttcaaa attagacaca acattgaaga tggaagcgtt   3240
caactagcag accattatca acaaaatact ccaattggcg atggccctgt ccttttacca   3300
gacaaccatt acctgtccac acaatctgcc ctttcgaaag atcccaacga aaagagagac   3360
cacatggtcc ttcttgagtt tgtaacagct gctgggatta cacatggcat ggatgaacta   3420
tacaaataat aatactagag ccaggcatca aataaaacga aaggctcagt cgaaagactg   3480
ggcctttcgt tttatctgtt gtttgtcggt gaacgctctc tactagagtc acactggctc   3540
accttcgggt gggcctttct gcgtttata                                    3569
```

<210> SEQ ID NO 6
<211> LENGTH: 1209
<212> TYPE: DNA
<213> ORGANISM: Artificial Sequence
<220> FEATURE:
<223> OTHER INFORMATION: Synthetic Polynucleotide

<400> SEQUENCE: 6
aaagaggaga aatactagat gaaatctaac aatgcgctca tcgtcatcct cggcaccgtc 60
accctggatg ctgtaggcat aggcttggtt atgccggtac tgccgggcct cttgcgggat 120
atcgtccatt ccgacagcat cgccagtcac tatggcgtgc tgctagcgct atatgcgttg 180
atgcaatttc tatgcgcacc cgttctcgga gcactgtccg accgctttgg ccgccgccca 240
gtcctgctcg cttcgctact tggagccact atcgactacg cgatcatggc gaccacaccc 300
gtcctgtgga tcctctacgc cggacgcatc gtggccggca tcaccggcgc cacaggtgcg 360
gttgctggcg cctatatcgc cgacatcacc gatggggaag atcgggctcg ccacttcggg 420
ctcatgagcg cttgtttcgg cgtgggtatg gtggcaggcc ccgtggccgg gggactgttg 480
ggcgccatct ccttgcatgc accattcctt gcggcggcgg tgctcaacgg cctcaaccta 540
ctactgggct gcttcctaat gcaggagtcg cataagggag agcgtcgacc gatgcccttg 600
agagccttca acccagtcag ctccttccgg tgggcgcggg gcatgactat cgtcgccgca 660
cttatgactg tcttctttat catgcaactc gtaggacagg tgccggcagc gctctgggtc 720
attttcggcg aggaccgctt tcgctggagc gcgacgatga tcggcctgtc gcttgcggta 780
ttcggaatct tgcacgccct cgctcaagcc ttcgtcactg gccccgccac caaacgtttc 840
ggcgagaagc aggccattat cgccggcatg gcggccgacg cgctgggcta cgtcttgctg 900
gcgttcgcga cgcgaggctg gatggccttc cccattatga ttcttctcgc ttccggcggc 960
atcgggatgc ccgcgttgca ggccatgctg tccaggcagg tagatgacga ccatcaggga 1020
cagcttcaag gatcgctcgc ggctcttacc agcctaactt cgatcattgg accgctgatc 1080
gtcacggcga tttatgccgc ctcggcgagc acatggaacg ggttggcatg gattgtaggc 1140
gccgccctat accttgtctg cctccccgcg ttgcgtcgcg gtgcatggag ccgggccacc 1200
tcgacctaa 1209

<210> SEQ ID NO 7
<211> LENGTH: 2017
<212> TYPE: DNA
<213> ORGANISM: Artificial Sequence
<220> FEATURE:
<223> OTHER INFORMATION: Synthetic Polynucleotide

<400> SEQUENCE: 7
tccctatcag tgatagagat tgacatccct atcagtgata gagatactga gcactactag 60
agaaagagga gaaatactag atgcgtaaag gagaagaact tttcactgga gttgtcccaa 120
ttcttgttga attagatggt gatgttaatg ggcacaaatt ttctgtcagt ggagagggtg 180
aaggtgatgc aacatacgga aaacttaccc ttaaatttat ttgcactact ggaaaactac 240
ctgttccatg gccaacactt gtcactactt tcggttatgg tgttcaatgc tttgcgagat 300
acccagatca tatgaaacag catgactttt tcaagagtgc catgcccgaa ggttatgtac 360
aggaaagaac tatatttttc aaagatgacg ggaactacaa gacacgtgct gaagtcaagt 420
ttgaaggtga tacccttgtt aatagaatcg agttaaaagg tattgatttt aaagaagatg 480
gaaacattct tggacacaaa ttggaataca actataactc acacaatgta tacatcatgg 540

```
cagacaaaca aaagaatgga atcaaagtta acttcaaaat tagacacaac attgaagatg    600
gaagcgttca actagcagac cattatcaac aaaatactcc aattggcgat ggccctgtcc    660
ttttaccaga caaccattac ctgtccacac aatctgccct ttcgaaagat cccaacgaaa    720
agagagacca catggtcctt cttgagtttg taacagctgc tgggattaca catggcatgg    780
atgaactata caaataataa tactagagaa agaggagaaa tactagatga aatctaacaa    840
tgcgctcatc gtcatcctcg gcaccgtcac cctggatgct gtaggcatag gcttggttat    900
gccggtactg ccgggcctct tgcgggatat cgtccattcc gacagcatcg ccagtcacta    960
tggcgtgctg ctagcgctat atgcgttgat gcaatttcta tgcgcacccg ttctcggagc   1020
actgtccgac cgctttggcc gccgcccagt cctgctcgct tcgctacttg gagccactat   1080
cgactacgcg atcatggcga ccacacccgt cctgtggatc ctctacgccg gacgcatcgt   1140
ggccggcatc accggcgcca caggtgcggt tgctggcgcc tatatcgccg acatcaccga   1200
tggggaagat cgggctcgcc acttcgggct catgagcgct tgtttcggcg tgggtatggt   1260
ggcaggcccc gtggccgggg gactgttggg cgccatctcc ttgcatgcac cattccttgc   1320
ggcggcggtg ctcaacggcc tcaacctact actgggctgc ttcctaatgc aggagtcgca   1380
taagggagag cgtcgaccga tgcccttgag agccttcaac ccagtcagct ccttccggtg   1440
ggcgcggggc atgactatcg tcgccgcact tatgactgtc ttctttatca tgcaactcgt   1500
aggacaggtg ccggcagcgc tctgggtcat tttcggcgag gaccgctttc gctggagcgc   1560
gacgatgatc ggcctgtcgc ttgcggtatt cggaatcttg cacgccctcg ctcaagcctt   1620
cgtcactggc cccgccacca aacgtttcgg cgagaagcag gccattatcg ccggcatggc   1680
ggccgacgcg ctgggctacg tcttgctggc gttcgcgacg cgaggctgga tggccttccc   1740
cattatgatt cttctcgctt ccggcggcat cgggatgccc gcgttgcagg ccatgctgtc   1800
caggcaggta gatgacgacc atcagggaca gcttcaagga tcgctcgcgg ctcttaccag   1860
cctaacttcg atcattggac cgctgatcgt cacggcgatt tatgccgcct cggcgagcac   1920
atggaacggg ttggcatgga ttgtaggcgc cgccctatac cttgtctgcc tccccgcgtt   1980
gcgtcgcggt gcatggagcc gggccacctc gacctaa                            2017
```

<210> SEQ ID NO 8
<211> LENGTH: 4649
<212> TYPE: DNA
<213> ORGANISM: Artificial Sequence
<220> FEATURE:
<223> OTHER INFORMATION: Synthetic Polynucleotide

<400> SEQUENCE: 8

```
tggtgcaaaa cctttcgcgg tatggcatga tagcgcctac tagagaaaga ggagaaatac     60
tagatgaaaa acataaatgc cgacgacaca tacagaataa ttaataaaat taaagcttgt    120
agaagcaata atgatattaa tcaatgctta tctgatatga ctaaaatggt acattgtgaa    180
tattatttac tcgcgatcat ttatcctcat tctatggtta aatctgatat ttcaatccta    240
gataattacc ctaaaaaatg gaggcaatat tatgatgacg ctaatttaat aaaatatgat    300
cctatagtag attattctaa ctccaatcat tcaccaatta attggaatat atttgaaaac    360
aatgctgtaa ataaaaaatc tccaaatgta attaaagaag cgaaaacatc aggtcttatc    420
actgggttta gtttccctat tcatacggct aacaatggct tcggaatgct tagttttgca    480
cattcagaaa aagacaacta tatagatagt ttatttttac atgcgtgtat gaacatacca    540
ttaattgttc cttctctagt tgataattat cgaaaaataa atatagcaaa taataaatca    600
```

```
aacaacgatt taaccaaaag agaaaaagaa tgtttagcgt gggcatgcga aggaaaaagc    660
tcttgggata tttcaaaaat attaggttgc agtgagcgta ctgtcacttt ccatttaacc    720
aatgcgcaaa tgaaactcaa tacaacaaac cgctgccaaa gtatttctaa agcaatttta    780
acaggagcaa ttgattgccc atactttaaa aattaataac actgatagtg ctagtgtaga    840
tcactactag agccaggcat caaataaaac gaaaggctca gtcgaaagac tgggcctttc    900
gttttatctg ttgtttgtcg gtgaacgctc tctactagag tcacactggc tcaccttcgg    960
gtgggccttt ctgcgtttat atactagaga cctgtaggat cgtacaggtt tacgcaagaa   1020
aatggtttgt tatagtcgaa taaatactag agaaagagga gaaatactag atggcttcct   1080
ccgaagacgt tatcaaagag ttcatgcgtt tcaaagttcg tatggaaggt tccgttaacg   1140
gtcacgagtt cgaaatcgaa ggtgaaggtg aaggtcgtcc gtacgaaggt acccagaccg   1200
ctaaactgaa agttaccaaa ggtggtccgc tgccgttcgc ttgggacatc ctgtccccgc   1260
agttccagta cggttccaaa gcttacgtta aacacccggc tgacatcccg gactacctga   1320
aactgtcctt cccggaaggt ttcaaatggg aacgtgttat gaacttcgaa gacggtggtg   1380
ttgttaccgt tacccaggac tcctccctgc aagacggtga gttcatctac aaagttaaac   1440
tgcgtggtac caacttcccg tccgacggtc cggttatgca gaaaaaaacc atgggttggg   1500
aagcttccac cgaacgtatg tacccggaag acggtgctct gaaaggtgaa atcaaaatgc   1560
gtctgaaact gaaagacggt ggtcactacg acgctgaagt taaaaccacc tacatggcta   1620
aaaaaccggt tcagctgccg ggtgcttaca aaaccgacat caaactggac atcacctccc   1680
acaacgaaga ctacaccatc gttgaacagt acgaacgtgc tgaaggtcgt cactccaccg   1740
gtgcttaata acgctgatag tgctagtgta gatcgctact agagaaagag gagaaatact   1800
agatgtccag attagataaa agtaaagtga ttaacagcgc attagagctg cttaatgagg   1860
tcggaatcga aggtttaaca acccgtaaac tcgcccagaa gctaggtgta gagcagccta   1920
cattgtattg gcatgtaaaa aataagcggg ctttgctcga cgccttagcc attgagatgt   1980
tagataggca ccatactcac ttttgccctt tagaagggga aagctggcaa gattttttac   2040
gtaataacgc taaaagtttt agatgtgctt tactaagtca tcgcgatgga gcaaaagtac   2100
atttaggtac acggcctaca gaaaaacagt atgaaactct cgaaaatcaa ttagcctttt   2160
tatgccaaca aggtttttca ctagagaatg cattatatgc actcagcgct gtggggcatt   2220
ttactttagg ttgcgtattg gaagatcaag agcatcaagt cgctaaagaa gaaagggaaa   2280
cacctactac tgatagtatg ccgccattat tacgacaagc tatcgaatta tttgatcacc   2340
aaggtgcaga gccagccttc ttattcggcc ttgaattgat catatgcgga ttagaaaaac   2400
aacttaaatg tgaaagtggg tccgctgcaa acgacgaaaa ctacgcttta gtagcttaat   2460
aacactgata gtgctagtgt agatcactac tagagccagg catcaaataa aacgaaaggc   2520
tcagtcgaaa gactgggcct ttcgttttat ctgttgtttg tcggtgaacg ctctctacta   2580
gagtcacact ggctcacctt cgggtgggcc tttctgcgtt tatatactag agtccctatc   2640
agtgatagag attgacatcc ctatcagtga tagagatact gagcactact agagaaagag   2700
gagaaatact agatgcgtaa aggagaagaa cttttcactg gagttgtccc aattcttgtt   2760
gaattagatg gtgatgttaa tgggcacaaa ttttctgtca gtggagaggg tgaaggtgat   2820
gcaacatacg gaaaacttac ccttaaattt atttgcacta ctggaaaact acctgttcca   2880
tggccaacac ttgtcactac tttcggttat ggtgttcaat gctttgcgag atacccagat   2940
catatgaaac agcatgactt tttcaagagt gccatgcccg aaggttatgt acaggaaaga   3000
```

actatatttt tcaaagatga cgggaactac aagacacgtg ctgaagtcaa gtttgaaggt 3060
gatacccttg ttaatagaat cgagttaaaa ggtattgatt ttaaagaaga tggaaacatt 3120
cttggacaca aattggaata caactataac tcacacaatg tatacatcat ggcagacaaa 3180
caaaagaatg gaatcaaagt taacttcaaa attagacaca acattgaaga tggaagcgtt 3240
caactagcag accattatca acaaaatact ccaattggcg atggccctgt ccttttacca 3300
gacaaccatt acctgtccac acaatctgcc ctttcgaaag atcccaacga aaagagagac 3360
cacatggtcc ttcttgagtt tgtaacagct gctgggatta cacatggcat ggatgaacta 3420
tacaaataat aatactagag aaagaggaga aatactagat gaaatctaac aatgcgctca 3480
tcgtcatcct cggcaccgtc accctggatg ctgtaggcat aggcttggtt atgccggtac 3540
tgccgggcct cttgcgggat atcgtccatt ccgacagcat cgccagtcac tatggcgtgc 3600
tgctagcgct atatgcgttg atgcaatttc tatgcgcacc cgttctcgga gcactgtccg 3660
accgctttgg ccgccgccca gtcctgctcg cttcgctact tggagccact atcgactacg 3720
cgatcatggc gaccacaccc gtcctgtgga tcctctacgc cggacgcatc gtggccggca 3780
tcaccggcgc cacaggtgcg gttgctggcg cctatatcgc cgacatcacc gatggggaag 3840
atcgggctcg ccacttcggg ctcatgagcg cttgtttcgg cgtgggtatg gtggcaggcc 3900
ccgtggccgg gggactgttg ggcgccatct ccttgcatgc accattcctt gcggcggcgg 3960
tgctcaacgg cctcaaccta ctactgggct gcttcctaat gcaggagtcg cataagggag 4020
agcgtcgacc gatgcccttg agagccttca acccagtcag ctccttccgg tgggcgcggg 4080
gcatgactat cgtcgccgca cttatgactg tcttctttat catgcaactc gtaggacagg 4140
tgccggcagc gctctgggtc attttcggcg aggaccgctt tcgctggagc gcgacgatga 4200
tcggcctgtc gcttgcggta ttcggaatct tgcacgccct cgctcaagcc ttcgtcactg 4260
gccccgccac caaacgtttc ggcgagaagc aggccattat cgccggcatg gcggccgacg 4320
cgctgggcta cgtcttgctg gcgttcgcga cgcgaggctg gatggccttc cccattatga 4380
ttcttctcgc ttccggcggc atcgggatgc ccgcgttgca ggccatgctg tccaggcagg 4440
tagatgacga ccatcaggga cagcttcaag gatcgctcgc ggctcttacc agcctaactt 4500
cgatcattgg accgctgatc gtcacggcga tttatgccgc ctcggcgagc acatggaacg 4560
ggttggcatg gattgtaggc gccgccctat accttgtctg cctccccgcg ttgcgtcgcg 4620
gtgcatggag ccgggccacc tcgacctaa 4649

<210> SEQ ID NO 9
<211> LENGTH: 4118
<212> TYPE: DNA
<213> ORGANISM: Artificial Sequence
<220> FEATURE:
<223> OTHER INFORMATION: Synthetic Polynucleotide

<400> SEQUENCE: 9
tggtgcaaaa cctttcgcgg tatggcatga tagcgcctac tagagaaaga ggagaaatac 60
tagatgaaaa acataaatgc cgacgacaca tacagaataa ttaataaaat taaagcttgt 120
agaagcaata atgatattaa tcaatgctta tctgatatga ctaaaatggt acattgtgaa 180
tattatttac tcgcgatcat ttatcctcat tctatggtta aatctgatat ttcaatccta 240
gataattacc ctaaaaaatg gaggcaatat tatgatgacg ctaatttaat aaaatatgat 300
cctatagtag attattctaa ctccaatcat tcaccaatta attggaatat atttgaaaac 360
aatgctgtaa ataaaaaatc tccaaatgta attaaagaag cgaaaacatc aggtcttatc 420

-continued

```
actgggttta gtttccctat tcatacggct aacaatggct tcggaatgct tagttttgca    480
cattcagaaa aagacaacta tatagatagt ttatttttac atgcgtgtat gaacatacca    540
ttaattgttc cttctctagt tgataattat cgaaaaataa atatagcaaa taataaatca    600
aacaacgatt taaccaaaag agaaaaagaa tgtttagcgt gggcatgcga aggaaaaagc    660
tcttgggata tttcaaaaat attaggttgc agtgagcgta ctgtcacttt ccatttaacc    720
aatgcgcaaa tgaaactcaa tacaacaaac cgctgccaaa gtatttctaa agcaatttta    780
acaggagcaa ttgattgccc atactttaaa aattaataac actgatagtg ctagtgtaga    840
tcactactag agccaggcat caaataaaac gaaaggctca gtcgaaagac tgggcctttc    900
gttttatctg ttgtttgtcg gtgaacgctc tctactagag tcacactggc tcaccttcgg    960
gtgggccttt ctgcgtttat atactagaga cctgtaggat cgtacaggtt tacgcaagaa   1020
aatggtttgt tatagtcgaa taaatactag agaaagagga gaaatactag atggcttcct   1080
ccgaagacgt tatcaaagag ttcatgcgtt tcaaagttcg tatggaaggt tccgttaacg   1140
gtcacgagtt cgaaatcgaa ggtgaaggtg aaggtcgtcc gtacgaaggt acccagaccg   1200
ctaaactgaa agttaccaaa ggtggtccgc tgccgttcgc ttgggacatc ctgtccccgc   1260
agttccagta cggttccaaa gcttacgtta aacacccggc tgacatcccg gactacctga   1320
aactgtcctt cccggaaggt ttcaaatggg aacgtgttat gaacttcgaa gacggtggtg   1380
ttgttaccgt tacccaggac tcctccctgc aagacggtga gttcatctac aaagttaaac   1440
tgcgtggtac caacttcccg tccgacggtc cggttatgca gaaaaaaacc atgggttggg   1500
aagcttccac cgaacgtatg tacccggaag acggtgctct gaaaggtgaa atcaaaatgc   1560
gtctgaaact gaaagacggt ggtcactacg acgctgaagt taaaaccacc tacatggcta   1620
aaaaaccggt tcagctgccg ggtgcttaca aaaccgacat caaactggac atcacctccc   1680
acaacgaaga ctacaccatc gttgaacagt acgaacgtgc tgaaggtcgt cactccaccg   1740
gtgcttaata acgctgatag tgctagtgta gatcgctact agagaaagag gagaaatact   1800
agatgtccag attagataaa agtaaagtga ttaacagcgc attagagctg cttaatgagg   1860
tcggaatcga aggtttaaca acccgtaaac tcgcccagaa gctaggtgta gagcagccta   1920
cattgtattg gcatgtaaaa aataagcggg ctttgctcga cgccttagcc attgagatgt   1980
tagataggca ccatactcac ttttgccctt tagaagggga aagctggcaa gatttttac    2040
gtaataacgc taaaagtttt agatgtgctt tactaagtca tcgcgatgga gcaaaagtac   2100
atttaggtac acggcctaca gaaaaacagt atgaaactct cgaaaatcaa ttagcctttt   2160
tatgccaaca aggtttttca ctagagaatg cattatatgc actcagcgct gtggggcatt   2220
ttactttagg ttgcgtattg gaagatcaag agcatcaagt cgctaaagaa gaaagggaaa   2280
cacctactac tgatagtatg ccgccattat tacgacaagc tatcgaatta tttgatcacc   2340
aaggtgcaga gccagccttc ttattcggcc ttgaattgat catatgcgga ttagaaaaac   2400
aacttaaatg tgaaagtggg tccgctgcaa acgacgaaaa ctacgcttta gtagcttaat   2460
aacactgata gtgctagtgt agatcactac tagagccagg catcaaataa aacgaaaggc   2520
tcagtcgaaa gactgggcct ttcgttttat ctgttgtttg tcggtgaacg ctctctacta   2580
gagtcacact ggctcacctt cgggtgggcc tttctgcgtt tatatactag agtccctatc   2640
agtgatagag attgacatcc ctatcagtga tagagatact gagcactact agagaaagag   2700
gagaaatact agatgcgtaa aggagaagaa cttttcactg gagttgtccc aattcttgtt   2760
gaattagatg gtgatgttaa tgggcacaaa ttttctgtca gtggagaggg tgaaggtgat   2820
```

```
gcaacatacg gaaaacttac ccttaaattt atttgcacta ctggaaaact acctgttcca   2880

tggccaacac ttgtcactac tttcggttat ggtgttcaat gctttgcgag atacccagat   2940

catatgaaac agcatgactt tttcaagagt gccatgcccg aaggttatgt acaggaaaga   3000

actatatttt tcaaagatga cgggaactac aagacacgtg ctgaagtcaa gtttgaaggt   3060

gataccettg ttaatagaat cgagttaaaa ggtattgatt ttaaagaaga tggaaacatt   3120

cttggacaca aattggaata caactataac tcacacaatg tatacatcat ggcagacaaa   3180

caaaagaatg gaatcaaagt taacttcaaa attagacaca acattgaaga tggaagcgtt   3240

caactagcag accattatca acaaaatact ccaattggcg atggccctgt ccttttacca   3300

gacaaccatt acctgtccac acaatctgcc ctttcgaaag atcccaacga aaagagagac   3360

cacatggtcc ttcttgagtt tgtaacagct gctgggatta cacatggcat ggatgaacta   3420

tacaaataat aatactagag aaagaggaga aatactagat ggagaaaaaa atcactggat   3480

ataccaccgt tgatatatcc caatggcatc gtaaagaaca ttttgaggca tttcagtcag   3540

ttgctcaatg tacctataac cagaccgttc agctggatat tacggccttt ttaaagaccg   3600

taaagaaaaa taagcacaag ttttatccgg cctttattca cattcttgcc cgcctgatga   3660

atgctcatcc ggaatttcgt atggcaatga aagacggtga gctggtgata tgggatagtg   3720

ttcacccttg ttacaccgtt ttccatgagc aaactgaaac gttttcatcg ctctggagtg   3780

aataccacga cgatttccgg cagtttctac acatatattc gcaagatgtg gcgtgttacg   3840

gtgaaaacct ggcctatttc cctaaagggt ttattgagaa tatgtttttc gtctcagcca   3900

atccctgggt gagtttcacc agttttgatt taaacgtggc caatatggac aacttcttcg   3960

cccccgtttt caccatgggc aaatattata cgcaaggcga caaggtgctg atgccgctgg   4020

cgattcaggt tcatcatgcc gtttgtgatg gcttccatgt cggcagaatg cttaatgaat   4080

tacaacagta ctgcgatgag tggcagggcg gggcgtaa                          4118
```

<210> SEQ ID NO 10
<211> LENGTH: 1486
<212> TYPE: DNA
<213> ORGANISM: Artificial Sequence
<220> FEATURE:
<223> OTHER INFORMATION: Synthetic Polynucleotide

<400> SEQUENCE: 10

```
tccctatcag tgatagagat tgacatccct atcagtgata gagatactga gcactactag     60

agaaagagga gaaatactag atgcgtaaag gagaagaact tttcactgga gttgtcccaa    120

ttcttgttga attagatggt gatgttaatg ggcacaaatt ttctgtcagt ggagagggtg    180

aaggtgatgc aacatacgga aaacttaccc ttaaatttat ttgcactact ggaaaactac    240

ctgttccatg gccaacactt gtcactactt tcggttatgg tgttcaatgc tttgcgagat    300

acccagatca tatgaaacag catgactttt tcaagagtgc catgcccgaa ggttatgtac    360

aggaaagaac tatatttttc aaagatgacg ggaactacaa gacacgtgct gaagtcaagt    420

ttgaaggtga tacccttgtt aatagaatcg agttaaaagg tattgatttt aaagaagatg    480

gaaacattct tggacacaaa ttggaataca actataactc acacaatgta tacatcatgg    540

cagacaaaca aaagaatgga atcaaagtta acttcaaaat tagacacaac attgaagatg    600

gaagcgttca actagcagac cattatcaac aaaatactcc aattggcgat ggccctgtcc    660

ttttaccaga caaccattac ctgtccacac aatctgccct ttcgaaagat cccaacgaaa    720

agagagacca catggtcctt cttgagtttg taacagctgc tgggattaca catggcatgg    780
```

-continued

```
atgaactata caaataataa tactagagaa agaggagaaa tactagatgg agaaaaaaat    840

cactggatat accaccgttg atatatccca atggcatcgt aaagaacatt ttgaggcatt    900

tcagtcagtt gctcaatgta cctataacca gaccgttcag ctggatatta cggccttttt    960

aaagaccgta aagaaaaata agcacaagtt ttatccggcc tttattcaca ttcttgcccg   1020

cctgatgaat gctcatccgg aatttcgtat ggcaatgaaa gacggtgagc tggtgatatg   1080

ggatagtgtt cacccttgtt acaccgtttt ccatgagcaa actgaaacgt tttcatcgct   1140

ctggagtgaa taccacgacg atttccggca gtttctacac atatattcgc aagatgtggc   1200

gtgttacggt gaaaacctgg cctatttccc taaagggttt attgagaata tgtttttcgt   1260

ctcagccaat ccctgggtga gtttcaccag ttttgattta aacgtggcca atatggacaa   1320

cttcttcgcc cccgttttca ccatgggcaa atattatacg caaggcgaca aggtgctgat   1380

gccgctggcg attcaggttc atcatgccgt ttgtgatggc ttccatgtcg gcagaatgct   1440

taatgaatta caacagtact gcgatgagtg gcagggcggg gcgtaa                  1486
```

<210> SEQ ID NO 11
<211> LENGTH: 1775
<212> TYPE: DNA
<213> ORGANISM: Artificial Sequence
<220> FEATURE:
<223> OTHER INFORMATION: Synthetic Polynucleotide

<400> SEQUENCE: 11

```
tccctatcag tgatagagat tgacatccct atcagtgata gagatactga gcactactag     60

agaaagagga gaaatactag atgcgtaaag gagaagaact tttcactgga gttgtcccaa    120

ttcttgttga attagatggt gatgttaatg ggcacaaatt ttctgtcagt ggagagggtg    180

aaggtgatgc aacatacgga aaacttaccc ttaaatttat ttgcactact ggaaaactac    240

ctgttccatg gccaacactt gtcactactt tcggttatgg tgttcaatgc tttgcgagat    300

acccagatca tatgaaacag catgactttt tcaagagtgc catgcccgaa ggttatgtac    360

aggaaagaac tatatttttc aaagatgacg ggaactacaa gacacgtgct gaagtcaagt    420

ttgaaggtga tacccttgtt aatagaatcg agttaaaagg tattgatttt aaagaagatg    480

gaaacattct tggacacaaa ttggaataca actataactc acacaatgta tacatcatgg    540

cagacaaaca aaagaatgga atcaaagtta acttcaaaat tagacacaac attgaagatg    600

gaagcgttca actagcagac cattatcaac aaaatactcc aattggcgat ggccctgtcc    660

ttttaccaga caaccattac ctgtccacac aatctgccct ttcgaaagat cccaacgaaa    720

agagagacca catggtcctt cttgagtttg taacagctgc tgggattaca catggcatgg    780

atgaactata caaataataa tactagagct gatccttcaa ctcagcaaaa gttcgattta    840

ttcaacaaag ccacgttgtg tctcaaaatc tctgatgtta cattgcacaa gataaaaata    900

tatcatcatg aacaataaaa ctgtctgctt acataaacag taatacaagg ggtgttatga    960

gccatattca acgggaaacg tcttgctccc gtccgcgctt aaactccaac atggacgctg   1020

atttatatgg gtataaatgg gctcgcgata atgtcgggca atcaggtgcg acaatctatc   1080

gcttgtatgg gaagcccgat gcgccagagt tgtttctgaa acatggcaaa ggtagcgttg   1140

ccaatgatgt tacagatgag atggtccgtc tcaactggct gacggagttt atgcctctcc   1200

cgaccatcaa gcattttatc cgtactcctg atgatgcgtg gttactcacc accgcgattc   1260

ctgggaaaac agccttccag gtattagaag aatatcctga ttcaggtgaa aatattgttg   1320

atgcgctggc cgtgttcctg cgccggttac attcgattcc tgtttgtaat tgtcctttta   1380
```

-continued

```
acagcgatcg tgtatttcgt cttgctcagg cgcaatcacg catgaataac ggtttggttg   1440

atgcgagtga ttttgatgac gagcgtaatg gctggcctgt tgaacaagtc tggaaagaaa   1500

tgcacaagct cttgccattc tcaccggatt cagtcgtcac tcatggtgat ttctcacttg   1560

ataaccttat ttttgacgag gggaaattaa taggttgtat tgatgttgga cgggtcggaa   1620

tcgcagaccg ttaccaggac cttgccattc tttggaactg cctcggtgag ttttctcctt   1680

cattacagaa acggcttttt caaaaatatg gtattgataa tcctgatatg aataaattgc   1740

agtttcattt gatgctcgat gagtttttct aataa                              1775


<210> SEQ ID NO 12
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 12

agccaactta aattaatgaa aaaatgttat taatcgttga gaattcgcgg ccgcttctag     60


<210> SEQ ID NO 13
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 13

taacttattg cgatatggtt acattaaggg caaagcatct ctgcagcggc cgctactagt     60


<210> SEQ ID NO 14
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 14

tgaccatgat tacggattca ctggccgtcg ttttacaacg tcgtggaatt cgcggccgct     60

tctag                                                                 65


<210> SEQ ID NO 15
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 15

gtgctgcaag gcgattaagt tgggtaacgc cagggttttc ccagtctgca gcggccgcta     60

ctagt                                                                 65


<210> SEQ ID NO 16
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
```

<220> FEATURE:
<221> NAME/KEY: misc_feature
<222> LOCATION: (88)..(90)
<223> OTHER INFORMATION: Phosphorothioate internucleotide bonds

<400> SEQUENCE: 16
tggatatacc accgttgata tatcccaatg gcatcgtaaa gaacattttg aggcatttca 60
gtcagttgct caatgtacct ataaccagac 90

<210> SEQ ID NO 17
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 17
agtgctcatc attggaaaac gttcttcggg gcgaaaactc tcaaggatct taccgctgtt 60
gagatccagt tcgatgtaac ccactcgtgc 90

<210> SEQ ID NO 18
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 18
taacaatttc acacaggaaa cagctatgac catgattacg gattcactgg ccgtcgtttt 60
acaacgtcgt gactgagaaa accctggcgt 90

<210> SEQ ID NO 19
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 19
agtgctcatc attggaaaac gttcttcggg gcgaaaactc tcaaggatct taccgctgtt 60
gagatccagt tcgatgtaac ccactcgtgc 90

-continued

<210> SEQ ID NO 20
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 20
tggatatacc accgttgata tatcccaatg gcatcgtaaa gaacattttg aggcatttca 60
gtcagttgct caatgtacct ataaccagac 90

<210> SEQ ID NO 21
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 21 taacttga 8

<210> SEQ ID NO 22
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 22 ttttatac 8

<210> SEQ ID NO 23
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 23
agcctgcttt 10

<210> SEQ ID NO 24
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 24 tttatac 7

<210> SEQ ID NO 25
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 25 tttgtac 7

<210> SEQ ID NO 26
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 26 cttatac 7

<210> SEQ ID NO 27
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 27 attatac 7

<210> SEQ ID NO 28
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 28 tctatac 7

<210> SEQ ID NO 29
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 29 tgtatac 7

<210> SEQ ID NO 30
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 30 ttcgtac 7

<210> SEQ ID NO 31
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 31 ttggtac 7

<210> SEQ ID NO 32
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 32 ttaatac 7

<210> SEQ ID NO 33
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 33
gacttaagag tctatcaccc ctagggccct ttcccggata taaacgccag gttgaatccg 60
cattt 65

<210> SEQ ID NO 34
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 34
ggagctacga tggatgagtc tgggtggagc gcgccccatt tataccgtga gtagggtcga 60
ccaag 65

<210> SEQ ID NO 35
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 35
aaccgcaaga tgcgtcggtg tacaaataat tgtcaacaga ccgtcgtgtt ttgaaaatgg 60
tacca 65

<210> SEQ ID NO 36
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 36
gcatcttcgg gcggtctcaa tcaagcatgg attacggtgt ttactctgtc ctgcggttac 60
ccatg 65

<210> SEQ ID NO 37
<211> LENGTH: 90
<212> TYPE: DNA
<213> ORGANISM: Artificial Sequence
<220> FEATURE:
<223> OTHER INFORMATION: Synthetic Oligonucleotide

<400> SEQUENCE: 37
gcatcgtaaa gaacattttg aggcatttca gtcagttgct caatgtacct ataaccagac 60
cgttcagctg gatattacgg cctttttaaa 90

<210> SEQ ID NO 38
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 38
gctaatcgaa ctgggcgaga gatcccagcg ctgatgcact cgatcccgag gcctgacccg 60
acata 65

<210> SEQ ID NO 39
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 39
tcagctcaga ctagagcggg gctgttgacg tttggggttg aaaaaatcta ttgtaccaat 60
cggct 65

<210> SEQ ID NO 40
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 40 cctgcttt 8

<210> SEQ ID NO 41
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 41
taagttggca 10

<210> SEQ ID NO 42
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 42 tcagcttt 8

<210> SEQ ID NO 43
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 43
taacttgagc 10

<210> SEQ ID NO 44
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 44
gacttaagag tctatcaccc ctagggccct ttcccggata taaacgccag gttgaatccg 60
catttcctgc tttattatac taagttggca 90

<210> SEQ ID NO 45
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 45
tcagctttct tatactaact tgagcggagc tacgatggat gagtctgggt ggagcgcgcc 60
ccatttatac cgtgagtagg gtcgaccaag 90

<210> SEQ ID NO 46
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 46
tcagctttat tatactaact tgagcaaccg caagatgcgt cggtgtacaa ataattgtca 60
acagaccgtc gtgttttgaa aatggtacca 90

<210> SEQ ID NO 47
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: Phosphorothioate internucleotide bonds
<220> FEATURE:
<221> NAME/KEY: misc_feature
<222> LOCATION: (88)..(90)
<223> OTHER INFORMATION: Phosphorothioate internucleotide bonds

<400> SEQUENCE: 47
gcatcttcgg gcggtctcaa tcaagcatgg attacggtgt ttactctgtc ctgcggttac 60
ccatgcctgc tttcttatac taagttggca 90

<210> SEQ ID NO 48
<211> LENGTH: 90
<212> TYPE: DNA
<213> ORGANISM: Artificial Sequence
<220> FEATURE:
<223> OTHER INFORMATION: Synthetic Oligonucleotide

<400> SEQUENCE: 48
gagaagaact tttcactgga gttgtcccaa ttcttgttga attagatggt gatgttaatg 60
ggcacaaatt ttctgtcagt ggagagggtg 90

<210> SEQ ID NO 49
<211> LENGTH: 738
<212> TYPE: DNA
<213> ORGANISM: Artificial Sequence
<220> FEATURE:
<223> OTHER INFORMATION: Synthetic Polynucleotide

<400> SEQUENCE: 49
aaagaggaga aatactagat gcgtaaagga gaagaacttt tcactggagt tgtcccaatt 60
cttgttgaat tagatggtga tgttaatggg cacaaatttt ctgacagtgg agagggtgaa 120
ggtgatgcaa catacggaaa acttaccctt aaatttattt gcactactgg aaaactacct 180
gttccatggc caacacttgt cactactttc ggttatggtg ttcaatgctt tgcgagatac 240
ccagatcata tgaaacagca tgactttttc aagagtgcca tgcccgaagg ttatgtacag 300
gaaagaacta tatttttcaa agatgacggg aactacaaga cacgtgctga agtcaagttt 360
gaaggtgata cccttgttaa tagaatcgag ttaaaaggta ttgattttaa agaagatgga 420
aacattcttg gacacaaatt ggaatacaac tataactcac acaatgtata catcatggca 480
gacaaacaaa agaatggaat caaagttaac ttcaaaatta gacacaacat tgaagatgga 540
agcgttcaac tagcagacca ttatcaacaa aatactccaa ttggcgatgg ccctgtcctt 600
ttaccagaca accattacct gtccacacaa tctgcccttt cgaaagatcc caacgaaaag 660
agagaccaca tggtccttct tgagtttgta acagctgctg ggattacaca tggcatggat 720
gaactataca aataataa 738

<210> SEQ ID NO 50
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 50
acctgtagga tcgtacaggt ttacgcaaga aaatggtttg ttatagtcga atacctctgg 60
cggtgata 68

-continued

```
<210> SEQ ID NO 51
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 51

aattgtgagc ggataacaat tgacattgtg agcggataac aagatactga gcaca          55


<210> SEQ ID NO 52
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 52

ttgacaaaca agatacattg tatgaaaata caagaaagtt tgttga                    46


<210> SEQ ID NO 53
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 53

acctgtagga tcgtacaggt ttacgcaaga aaatggtttg ttatagtcga ataaa          55


<210> SEQ ID NO 54
<211> LENGTH: 116
<212> TYPE: DNA
<213> ORGANISM: Artificial Sequence
<220> FEATURE:
<223> OTHER INFORMATION: Synthetic Oligonucleotide

<400> SEQUENCE: 54

gcgcaacgca attaatgtga gttagctcac tcattaggca taacaccgtg cgtgttgact     60

attttacctc tggcggtgat aatgtgtgga attgtgagcg gataaaattt cacaca        116


<210> SEQ ID NO 55
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 55

acctgtagga tcgtacaggt ttacttgtga gcggataaca atatagtgtg tggaattgtg     60

agcggataac aatt                                                       74
```